US010526374B2

(12) United States Patent
Kondo et al.

(10) Patent No.: US 10,526,374 B2
(45) Date of Patent: *Jan. 7, 2020

(54) FACTOR INVOLVED IN LATENT INFECTION WITH HERPESVIRUS, AND USE THEREOF

(71) Applicants: Virus Ikagaku Kenkyusho Inc., Osaka (JP); Japan Tobacco Inc., Tokyo (JP)

(72) Inventors: Kazuhiro Kondo, Tokyo (JP); Nobuyuki Kobayashi, Tokyo (JP)

(73) Assignees: VIRUS IKAGAKU KENKYUSHO INC., Osaka (JP); JAPAN TOBACCO INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/756,858

(22) Filed: Feb. 1, 2013

(65) Prior Publication Data

US 2013/0137088 A1 May 30, 2013

Related U.S. Application Data

(62) Division of application No. 12/679,816, filed as application No. PCT/JP2008/067300 on Sep. 25, 2008, now Pat. No. 8,431,352.

(30) Foreign Application Priority Data

Sep. 27, 2007 (JP) ................ 2007-250461

(51) Int. Cl.
| | |
|---|---|
| *C12N 15/38* | (2006.01) |
| *C12N 15/63* | (2006.01) |
| *C12N 15/79* | (2006.01) |
| *C12N 7/01* | (2006.01) |
| *C12N 5/10* | (2006.01) |
| *C07K 14/005* | (2006.01) |
| *C07K 14/03* | (2006.01) |
| *C12N 15/11* | (2006.01) |
| *C12N 7/00* | (2006.01) |
| *G01N 33/68* | (2006.01) |

(52) U.S. Cl.
CPC ........... *C07K 14/005* (2013.01); *C07K 14/03* (2013.01); *C12N 5/10* (2013.01); *C12N 7/00* (2013.01); *C12N 15/11* (2013.01); *C12N 15/63* (2013.01); *C12N 15/79* (2013.01); *G01N 33/6854* (2013.01); *G01N 33/6893* (2013.01); *G01N 33/6896* (2013.01); *A01K 2267/0356* (2013.01); *C12N 2710/10343* (2013.01); *C12N 2710/16522* (2013.01); *C12N 2710/16571* (2013.01); *C12N 2740/10043* (2013.01); *G01N 2333/035* (2013.01); *G01N 2800/304* (2013.01)

(58) Field of Classification Search
None
See application file for complete search history.

(56) References Cited

U.S. PATENT DOCUMENTS

2008/0280283 A1   11/2008   Kondo

FOREIGN PATENT DOCUMENTS

WO   WO 2006/006634 A1   1/2006

OTHER PUBLICATIONS

Rudinger. In "Peptide Hormones" (ed. J.A. Parsons) University Park Press, Baltimore, pp. 1-7 (1976).*
Japanese Office Action issued in Japanese Patent Application No. 2013-063090 dated Sep. 2, 2014.
Mirandola et al., "Temporal Mapping of Transcripts in Herpesvirus 6 Variants", Journal of Virology. vol. 72, No. 5 (1998) pp. 3837-3844.
Dominguez et al., "Human Herpesvirus 6B Genome Sequence: Coding with Human Herpesvirus 6A," Journal of Virology, vol. 73, No. 10, pp. 8040-8052, Oct. 1999.
Dominguez et al., "Human herpesvirus 6B genome sequence: coding content and comparison with human herpesvirus 6A", J. Virol, vol. 73, No. 10, 1999, pp. 8040-8052, XP002609118, Abstract only from Database Protein (Online) provided.
Extended European Search Report for Application No. 08833887.6 dated Dec. 21, 2010.
Japanese International Search Report dated Oct. 28, 2008 for corresponding International Application No. PCT/JP2008/067300.
Kobayashi et al., "Hito Herpesvirus (HHV)-6 Senpuku Kansen Tokuiteki Tanpaku ni yoru Utsu Shojo no Hassho Kijo," Dai 55 Kai The Japanese Society of Virology Gakujutsu Shukai Program, Shorokushu, p. 120, Oct. 1, 2007.
Kogelnik et al., "Use of valganciclovir in patients with elevated antibody titers against Human Herpesvirus-6 (HHV-6) and Epstein-Barr Virus (EBV) who were experiencing central nervous system dysfunction including long-standing fatigue", J. of Clinical Virology, vol. 37, Suppl. 1, pp. S33-S38, 2006.
Kondo et al., "Recognition of a Novel Stage of Betaherpesvirus Latency in Human Herpesvirus 6," Journal of Virology, vol. 77, No. 3, pp. 2258-2264, Feb. 2003.
Kondo et al., "Association of Human Herpesvirus 6 Infection of the Central Nervous System with Recurrence of Febrile Convulsions," The Journal of Infectious Diseases, vol. 167, pp. 1197-1200, 1993.
Kondo et al., "Identification of Human Herpesvirus 6 Latency-Associated Transcripts," Journal of Virology, vol. 76, No. 8, pp. 4145-4151, Apr. 2002.

(Continued)

*Primary Examiner* — Robert C Hayes
(74) *Attorney, Agent, or Firm* — Birch, Stewart, Kolasch & Birch, LLP

(57) ABSTRACT

Disclosed are a protein and a gene each of which is a factor involved in latent infection with a herpesvirus. An antibody against the factor was detected in approximately 50% of patients suffering from mental disorders, whereas the antibody was hardly detected in healthy persons. Further, a mouse having SITH-1 introduced therein developed a mental disorder such as a manic-depressive illness or depression-like disorder. Based on these findings, it is possible to provide a method for objectively determining a mental disorder and an animal model of a mental disorder.

9 Claims, 8 Drawing Sheets

Specification includes a Sequence Listing.

(56) References Cited

OTHER PUBLICATIONS

Kondo et al., Latent human herpesvirus 6 infection of human monocytes/macrophages, Journal of General Virology, vol. 72, pp. 1401-1408, 1991, Great Britain.
Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, 2006. 03, Heisei 17 Nendo Sokatsu•Buntan Kenkyu Hokokusho. pp. 19-23.
Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, 2007. 03, Heisei 18 Nendo Sokatsu•Buntan Kenkyu Hokokusho, pp. 13-18.
Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, 2008. 03, Heisei 19 Nendo Sokatsu•Buntan Kenkyu Hokokusho, pp. 17-23.
Kondo et al., "Identification of a novel HHV-6 latent-protein associated with CFS and mood disorders", Neuroscience Research, vol. 68S, p. e51, 2010, XP002609007.
Kondo, "Herpesvirus Kansen to Hiro," Virus, vol. 55, No. 1, pp. 9-17, 2005.
Kondo, "Hito Herpesvirus 6 (HHV-6) to CFS," Prog. Med., vol. 25, pp. 1315-1319, 2005.
Kondo, "Virus no Senpuku Kansen Tanpakushitsu to Hiro," Molecular Medicine, vol. 41, No. 10, pp. 1216-1221, 2004.
Patnaik et al., "Prevalence of IgM Antibodies to Human Herpesvirus 6 Early Antigen (p41/38) in Patients with Chronic Fatigue Syndrome", The Journal of Infectious Diseases, vol. 172, pp. 1364-1367, 1995, XP002609186.
Reeves et al., "Human Herpesviruses 6 and 7 in Chronic Fatigue Syndrome: A Case-Control Study", Clinical Infectious Diseases, vol. 31, pp. 48-52, 2000, XP002609184.
Wallace et al., "Human Herpesviruses in Chronic Fatigue Syndrome", Clinical and Diagnostic Laboratory Immunology, vol. 6, No. 2, pp. 216-223, Mar. 1999, XP002609185.
"Human herpesvirus 6B, complete genome," NCBI Database, Reference Sequence: NC_000898.1, Apr. 5, 2007, pp. 1-61.
Eymard et al., "Human herpesvirus 6 and chronic fatigue syndrome," Canadian Journal of Infectious Diseases, vol. 4, No. 4, Jul./Aug. 1993, pp. 199-202.
Genbank, Accession No. U92288.1, Nucleotide Database, Oct. 7, 2005, http://www.ncbi.nlm.nih.gov/nuccore/U92288.1, 12 pages provided.
New Zealand Office Action for Application No. 599590 dated Aug. 22, 2013.
U.S. Office Action, dated Apr. 21, 2016, for U.S. Appl. No. 13/732,981.
U.S. Office Action issued in U.S. Appl. No. 13/732,981 dated Oct. 21, 2016.
U.S. Office Action, dated Jun. 28, 2017, for Copending U.S. Appl. No. 15/462,031.
U.S. Office Action dated Jan. 29, 2018 for U.S. Appl. No. 15/462,031.
U.S. Advisory Action, dated Jun. 26, 2018, for Copending U.S. Appl. No. 15/462,031.
U.S. Office Action for U.S. Appl. No. 15/462,031, dated Dec. 14, 2018.

* cited by examiner

F I G. 1
mRNA during productive infection
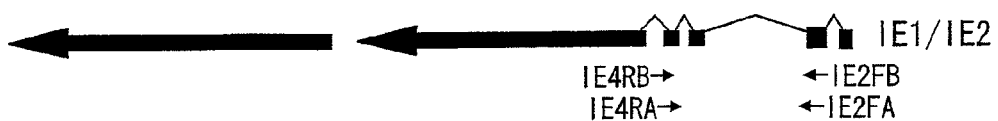
mRNA during latent infection
Sense transcripts
Antisense transcripts
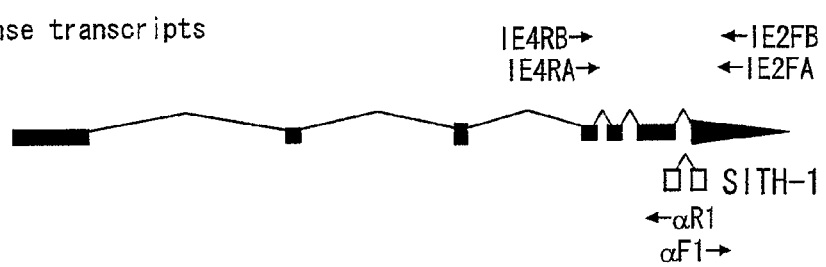

FACTOR INVOLVED IN LATENT INFECTION WITH HERPESVIRUS, AND USE THEREOF

This application is a Divisional of copending application Ser. No. 12/679,816 filed on Mar. 24, 2010 and for which priority is claimed under 35 U.S.C. § 120, which is a National Phase of PCT International Application No PCT/JP2008/067300, filed on Sep. 25, 2008, under 35 U.S.C. § 371, which claims priority under 35 U.S.C. 119(a) to Patent Application No. JP 2007-250461, filed on Sep. 27, 2007. The entire contents of all of the above applications are hereby expressly incorporated by reference into the present application.

TECHNICAL FIELD

The present invention relates to: a factor involved in latent infection with a herpesvirus; and use thereof. Particularly, the present invention relates to a novel protein which is specifically expressed during latent infection with a herpesvirus; a gene encoding said protein; and use thereof.

BACKGROUND ART

Viruses of the family Herpesviridae, each having an overall size of approximately 150 nm to 200 nm, are such that a core protein is surrounded by multi-stranded DNA with molecular masses of 80 to 150×10$^6$ daltons. This multi-stranded DNA is enclosed in an icosahedral capsid which has a diameter of approximately 100 nm and is made of 162 capsomers, so as to form a nucleocapsid which is surrounded by an envelope. Herpes viruses have been found in almost all mammals and amphibians. In particular, viruses of the family Herpesviridae that have host specificity for humans are named human herpesviruses (HHVs). HHVs are classified into subfamilies Alphaherpesvirinae (e.g., herpes simplex virus and varicella-zoster herpes virus), Betaherpesvirinae (e.g., cytomegalovirus), and Gammaherpesvirinae (e.g. EB virus).

These herpes viruses are characterized by having a stage of latent infection. The "latent infection" refers to such a state of infection that a virus that has infected a host cell does not produce infectious virions within the host cell but continues to survive. Even in this phase of latent infection, virus genes and gene products that help the virus genes to exist are retained within the host cell. Herpes viruses that exhibit latent infection are known to resume production of virions and viral replication in a large amount owing to certain causes on the side of the host (e.g. growing old and somatic complaints (including fatigue)). This state is called "reactivation".

In short, herpes viruses have the following unique character: Herpes viruses continue to infect the host latently as long as the host has nothing abnormal; however, once a somatic disturbance occurs in the host and the viruses detect that the host is in danger, the viruses are reactivated to seek another, healthy host.

To study the biology of such viruses of the family Herpesviridae, understanding their latent infection and reactivation is essential. However, among the many herpes viruses, it is only EB virus belonging to the subfamily Gammaherpesvirinae that has been studied to yield many findings about latent infection, and much remains unclear about other viruses.

In particular, concerning factors that may be involved in latent infection of Betaherpesvirinae, there has been obtained no information other than from the findings previously made by the present inventors. For example, Non-Patent Document 1 discloses latent infection of HHV-6 in macrophages in peripheral blood which macrophages have differentiated to a relatively high extent, and identifies the sites in a host at which sites the host is latently infected with HHV-6. Non-Patent Document 2 describes very frequent invasion of HHV-6 into a brain upon primary infection to cause persistent infection and latent infection. Non-Patent Document 3 discloses genes (latent infection genes) that are expressed during latent infection of HHV-6, and suggests that those genes play the role of regulating latent infection and reactivation of the virus.

Non-Patent Document 4 shows that the state of latent infection with HHV-6 involves an intermediate stage which is comparatively stable and allows for active gene expression, with the result that a latent infection gene and a protein (latent infection gene protein) encoded by this gene are expressed abundantly. What is more, Non-Patent Document 5 shows that patients with chronic fatigue syndrome had in their sera antibodies against latent infection gene proteins which are expressed at an increased level in the intermediate stage.

Non-Patent Document 1
Kondo. K et al. Ltatent human herpesvirus 6 infection of human monocytes/macrophages (J Gen Virol 72:1401-1408, 1991)
Non-Patent Document 2
Kondo. K et al. Association of human herpesvirus 6 infection of the central nervous system with recurrence of febrile convulsions. (J Infect Dis 167:1197-1200, 1993.)
Non-Patent Document 3
Kondo. K et al. Identification of human herpesvirus 6 latency-associated transcripts. (J. Virol. 76: 4145-4151, 2002)
Non-Patent Document 4
Kondo K et al. Recognition of a Novel Stage of Beta-Herpesvirus Latency in Human Herpesvirus 6. (J. Virol. 77: 2258-2264, 2003)
Non-Patent Document 5
Kazuhiro Kondo, "*Herpesvirus Kansen to Hiro* (Herpesvirus latency and fatigue)", Virus, 2005, Vol. 55, No. 1, pages 9 to 18

SUMMARY OF INVENTION

However, there has not been identified any latent infection gene or latent infection gene protein specifically involved in diseases. In addition, its functions and a relationship with a pathogenic mechanism of chronic fatigue syndrome have remained unknown. Further, there is a possibility that HHV-6 is involved in other diseases in addition to chronic fatigue syndrome.

Therefore, it has been strongly demanded to make clear the relationship between infection with HHV-6 and diseases, and also to develop a technique contributing to establishment of (i) an objective diagnosis method for diseases and (ii) an animal model.

The present invention was made in view of the foregoing problems, and an object of the present invention is to identify a factor involved in latent infection with HHV-6 and to provide use thereof.

In order to solve the foregoing problems, the present inventors made a diligent study. As a result, the present inventors reached the following unique idea: In light of the HHV-6's distinctive nature, i.e., the latent infection and the reactivation, identifying a factor involved in the latent infection and the reactivation would yield a finding about the relationship between infection with HHV-6 and mental disorders. Based on this idea, the present inventors conducted complicated, sophisticated experiences many times. As a result, the present inventors identified: a novel gene expressed at the intermediate stage, at which a gene specific for latent infection with HHV-6 is expressed actively; and a novel protein (Small protein encoded by the Intermediate Transcript of HHV-6-1; SITH-1) encoded by the novel gene. Further, the present inventors conducted functional analysis of the novel gene and the protein SITH-1, which is encoded by the novel gene, so as to make the following new findings: (i) the protein SITH-1 has ability to increase an intracellular calcium concentration; and (ii) an antibody against the protein SITH-1 is significantly detected in patients with mood disorders, but is hardly detectable in healthy persons. Thus, the present invention was completed. The present invention was completed based on the above new findings, and includes the following inventions:

(1) A gene encoding:
(a) a protein having the amino acid sequence shown in SEQ ID NO: 1; or
(b) a protein having an amino acid sequence with a substitution, deletion, insertion, and/or addition of one or several amino acids in the amino acid sequence shown in SEQ ID NO: 1, the protein having activity of increasing an intracellular calcium concentration.

(2) A gene including an open reading frame region having the nucleotide sequence shown in SEQ ID NO: 2.

(3) A gene encoding a protein that hybridizes under stringent hybridization conditions with DNA having a nucleotide sequence complementary to DNA having the nucleotide sequence shown in SEQ ID NO: 2 or 3, the protein having activity of increasing an intracellular calcium concentration.

(4) A protein encoded by a gene as set forth in any one of (1) through (3).

(5) A protein being:
(a) a protein having the amino acid sequence shown in SEQ ID NO: 1; or
(b) a protein having an amino acid sequence with a substitution, deletion, insertion, and/or addition of one or several amino acids in the amino acid sequence shown in SEQ ID NO: 1, the protein having activity of increasing an intracellular calcium concentration.

(6) An antibody that recognizes a protein as set forth in (4) or (5).

(7) A recombinant expression vector including a gene as set forth in any one of (1) through (3).

(8) A transformant which is produced by transfer of a gene as set forth in any one of (1) through (3) or a recombinant expression vector as set forth in (7).

(9) A gene detection instrument including a probe having at least part of a nucleotide sequence, or its complementary sequence, of a gene as set forth in any one of (1) through (3).

(10) A detection instrument including a probe which is a polypeptide having at least part of an amino acid sequence of a protein as set forth in (4) or (5).

(11) A determination method including the step of: determining whether or not an antibody as set forth in (6) exists in a subject.

(12) The determination method as set forth in (11), wherein: the determining is made by means of immunological detection through use of a protein as set forth in (4) or (5) or a partial fragment of the protein.

(13) The determination method as set forth in (11) or (12), wherein: the determining is made by using a biological sample isolated from the subject.

(14) A determination kit for performing a determination method as set forth in any one of (11) through (13).

(15) The determination kit as set forth in (14), including at least one selected from:
(i) a protein as set forth in (4) or (5);
(ii) a partial fragment of the protein (i); and
(iii) an instrument to which the protein (i) or the partial fragment (ii) is immobilized.

(16) A diagnosis method for diagnosing whether or not a human subject has a mental disorder, including the steps of: (i) determining whether or not an antibody as set forth in (6) exists in a human subject, according to a determination method as set forth in any one of (11) through (13); and (ii) determining that the human subject contracts chronic fatigue syndrome, in a case where the step (i) determines that the antibody as set forth in (6) exists in the human subject.

(17) The diagnosis method as set forth in (16), wherein: in the step (i), the determining is made by using a biological sample isolated from the human subject.

(18) A diagnosis method for diagnosing whether or not an animal subject has a mental disorder, including the steps of: (i) determining whether or not an antibody as set forth in (6) exists in an animal subject, according to a determination method as set forth in any one of (11) through (13); and (ii) determining that the animal subject has a mental disorder, in a case where the step (i) determines that the antibody as set forth in (6) exists in the animal subject.

(19) A diagnosis kit for performing a diagnosis method as set forth in any one of (16) through (18).

(20) The diagnosis kit as set forth in (19), including at least one selected from:
(i) a protein as set forth in (4) or (5);
(ii) a partial fragment of the protein (i); and
(iii) a detection instrument to which the protein (i) or the partial fragment (ii) is immobilized.

(21) An animal model determination method for determining whether or not an animal subject is useful as an animal model of a mental disorder, including the steps of: (i) diagnosing whether or not an animal subject has a mental disorder, according to a diagnosis method as set forth in (18); and (ii) determining that the animal subject is useful as an animal model of the mental disorder, in a case where the step (i) diagnoses that the animal subject has the mental disorder.

(22) An animal model produced by transfer of a gene as set forth in any one of (1) through (3), a gene product thereof, or a recombinant expression vector as set forth in (7).

(23) A screening method for performing screening for a candidate substance for a psychotropic agent, including the steps of: (i) administering, to an animal model of a mental disorder, a subject substance; (ii) determining whether or not the mental disorder of the animal model is cured or improved, according to a diagnosis method as set forth in (18); and (iii) determining that the subject substance is a candidate substance for a psychotropic agent, in a case where the metal disorder of the animal model is determined to be cured or improved.

It is more preferable that the screening method (23) is performed both by (i) the diagnosis method (18) and (ii) a diagnosis method using e.g., a (heretofore known) behavior disorder and/or startle response of an animal.

A gene or a protein of the present invention is expressed specifically during latent infection with a herpesvirus, and has ability to regulate latent infection and reactivation of a herpesvirus. Further, as described later, it has been shown that an antibody against a protein of the present invention is significantly found in patients with mental disorders. Therefore, determining the presence or absence of the antibody enables objective diagnosis for mental disorders.

Furthermore, a gene or a protein of the present invention is applicable to diagnosis for various diseases, as well as diagnosis for the diseases described herein. Moreover, a gene or a protein of the present invention is also available for use in drug screening methods, animal model producing methods, and various kinds of kits, for example.

For a fuller understanding of the nature and advantages of the invention, reference should be made to the ensuing detailed description taken in conjunction with the accompanying drawings.

BRIEF DESCRIPTION OF DRAWINGS

FIG. 1 is a diagram showing schematically a structure of a latent infection specific gene and positions of analytical primers.

DESCRIPTION OF EMBODIMENTS

Figure 2:
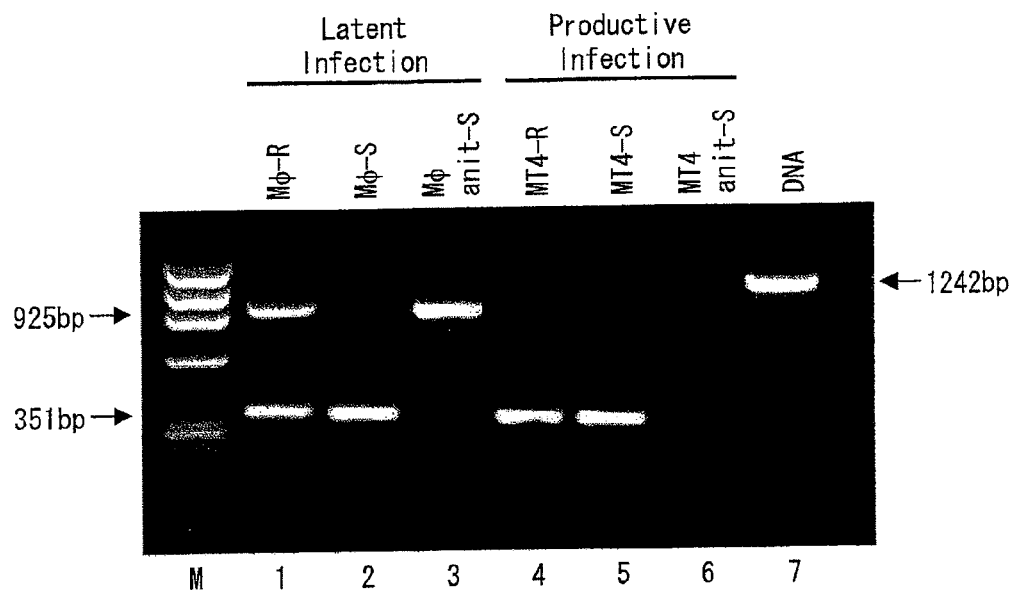
FIG. 2 is a diagram showing the results of amplification performed by the PCR technique with respect to HHV-6 gene products.

The following describes one embodiment of the present invention. However, the present invention is not limited to this.

First, to help understanding of the present invention, how the present inventors completed the present invention will be described briefly. The present inventors speculated that infection with HHV-6 among the various kinds of human herpes viruses was most probably a cause of mental disorders, particularly ones accompanied by mood disorders. The reasons include: (i) among symptoms of chronic fatigue syndrome (CFS) for which HHV-6 has heretofore been held as one cause, depressive symptoms and others that are often found in mental disorders are recognized; (ii) HHV-6 causes latent infection in a brain; and (iii) an antibody reactive with the heretofore identified HHV-6 latent infection specific gene protein, as well as an antibody reactive with an unknown protein that was expressed in cells latently infected with HHV-6 but which was yet to be identified for a gene or for itself were detected at high frequencies in the sera of CFS patients.

Further, in light of the fact that the primary sites in a brain which are latently infected with HHV-6 include a frontal lobe and a hippocampal region each of which governs human thoughts and emotions, as well as the fact that viruses causing latent infection in a brain are just a few including HHV-6, the present inventors speculated the relationship between HHV-6 and mental disorders. Furthermore, HHV-6 is known to cause latent infection in glial cells (e.g., astrocytes) that play important roles in metabolism of substances within a brain (e.g., serotonin) that are associated with depression. Also in terms of this, the present inventors reached the unique idea that HHV-6 might be associated with mental disorders such as mood disorders.

Thus, the present inventors speculated that patients with CFS might include considerable cases who present with psychiatric symptoms on account of the latent infection of the brain with HHV-6. In particular, the present inventors speculated the relationship between HHV-6 and mood disorders such as depression and manic-depressive illness.

Mood disorders are symptoms found in mental disorders such as depression and manic-depressive illness, and two most typical examples are depression that presents with only symptoms of depression and manic-depressive illness in which episodes of mania alternate with episodes of depression. While various possible causes have been proposed, including stress, genetic aberrations, and infection, no single factor has yet been established. The incidence of mood disorders is increasing these days, and this is becoming a big social problem. Therefore, it is desirable that the etiology and pathology of each mood disorder are unraveled and methods for diagnosing and treating it are developed as soon as possible. A problem worth particular mention here is that diagnosis of mood disorders is liable to be only qualitative, and involves difficulty in achieving objectivity. In addition, animal models contributing to studies of mood disorders and development of methods for treating them have not been developed adequately. This hinders clarification of the etiology and development of the treating methods.

On this account, the present inventors thought that it necessary to make clear the relationship between (i) infection with HHV-6 and (ii) mood disorders and mental disorders, and to develop a technique contributing to establishment of objective diagnosis and animal models for mood disorders and mental disorders.

Needless to say, these speculations are unique ones at which the present inventors arrived as a result of a diligent study made in this research field for a long time, and cannot be easily arrived at by a general person skilled in the art.

The following describes details of a protein, a gene, and others of the present invention in order.

(1) Protein and Gene of the Present Invention (1-1) Structure

The present invention provides a factor that is involved in latent infection with a herpes virus. In greater detail, the present invention provides (i) a protein that is expressed specifically during latent infection with a herpes virus and (ii) a gene encoding the protein. The phrase reading "expressed specifically during latent infection with a herpes virus" means that a gene derived from a herpes virus or a gene product thereof is expressed specifically in a virally infected host while the host is latently infected (but not productively infected) with the herpes virus.

The protein and the gene may be, for example, (a) a protein having the amino acid sequence shown in SEQ ID NO: 1 and a gene encoding the protein.

As will be described later in the Example, the protein having the amino acid sequence shown in SEQ ID NO: 1 is isolated and identified as a protein that is expressed specifically during latent infection with human herpesvirus-6 (HHV-6). This protein is hereinafter referred to as "Small protein encoded by the Intermediate Transcript of HHV-6-1 (protein SITH-1)". The protein SITH-1 is a protein which has a molecular mass of approximately 17.5 kDa, the amino acid sequence shown in SEQ ID NO: 1, and 159 amino acids.

The protein SITH-1 is encoded by an SITH-1 gene. As shown in SEQ ID NO: 3, cDNA of the SITH-1 gene has a size of 1795 base pairs (approximately 1.79 kbp). Further, the $954^{th}$ to $956^{th}$ nucleotide sequence represents a start codon (Kozak ATG), whereas the $1431^{st}$ to $1433^{rd}$ nucleotide sequence represents a stop codon (TAA). Hence, the SITH-1 gene has an open reading frame (ORF) having the $954^{th}$ to $1430^{th}$ nucleotide sequence of the nucleotide sequence shown in SEQ ID NO: 3, with the ORF having a size of 477 base pairs (approximately 0.48 kbp). The nucleotide sequence that represents the ORF region of the cDNA of SITH-1 is shown in SEQ ID NO: 2. Note that the nucleotide sequence shown in SEQ ID NO: 2 includes three bases of the stop codon.

The protein of the present invention may be, for example, (b) a protein having an amino acid sequence with a substitution, deletion, insertion, and/or addition of one or several amino acids in the amino acid sequence shown in SEQ ID NO: 1, the protein being expressed specifically during latent infection with a herpes virus. The gene of the present invention may be, for example, a gene encoding this protein.

The phrase reading "with a substitution, deletion, insertion, and/or addition of one or several amino acids" means substitution, deletion, insertion, and/or addition of numbers of amino acids (for example, preferably 10 or less, more preferably 7 or less, further preferably 5 or less) that can be brought about by a known mutant peptide producing method such as site-directed mutagenesis. Thus, the protein (b) may be described as being a mutant protein of the protein (a). Note that the "mutant" herein primarily refers to a mutant made by artificial introduction by means of a known mutant protein producing method, or may be one obtained by isolation and purification of a naturally-existing, similar mutant protein.

Alternatively, the gene of the present invention may be, for example, a gene encoding (c) a protein that hybridizes under stringent hybridization conditions with DNA having a nucleotide sequence complementary to DNA having the nucleotide sequence shown in SEQ ID NO: 2, the protein being expressed specifically during latent infection with a herpes virus.

The phrase reading "hybridizes under stringent hybridization conditions" means that hybridization occurs only in a case where nucleotide sequences of interest have at least 90% identity, preferably at least 95% identity, most preferably at least 97% identity. As a specific example of the "stringent hybridization conditions", the following condition is possible: A hybridization filter is incubated overnight at 42° C. in a hybridization solution (including 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA), followed by being washed in 0.1×SSC at approximately 65° C. Further, the hybridization can be performed by a conventionally-known method, for example, according to the procedures described in "J. Sambrook et al. Molecular Cloning, A Laboratory Manual, 2d Ed., Cold Spring Harbor Laboratory (1989)", and is not limited to any specific one. Generally, as the temperature rises and the salt concentration becomes lower, the level of the stringency increases (i.e., more difficult to hybridize).

Note that the term "gene" herein is used interchangeably with "polynucleotide", "nucleic acid" or "nucleic acid molecule". The "polynucleotide" refers to a polymer of nucleotides. Thus, the term "gene" herein includes not only double-stranded DNA but also single-stranded DNAs (e.g., a sense strand and an antisense strand constituting the double-stranded DNA) and RNA (e.g., mRNA). The antisense strand may be used as a probe or an antisense drug. The term "DNA" includes e.g., (i) cDNA obtained by cloning, a chemical synthesis technique, or a combination thereof and (ii) a genomic DNA. That is, the "DNA" may be a "genomic" DNA including a noncoding sequence (e.g., intron), which genomic DNA is a form contained in animal genomes. Alternatively, the "DNA" may be cDNA obtained from mRNA by using reverse transcriptase or polymerase, i.e., "transcriptional" DNA including no noncoding sequence (e.g., intron). Further, the gene of the present invention may be one having not only a sequence encoding the amino acid described concerning the above (a) or (b) but also a sequence of an untranslated region (UTR) and/or a vector sequence (including an expression vector sequence). Further, the mRNA or the cDNA may include, at an end and/or the inside of its translated region, a desired polynucleotide such as a regulatory sequence or a polyadenylic acid sequence. Furthermore, in a case where the protein of the present invention can be encoded by a plurality of alleles, the term "nucleic acid" encompasses all of the alleles, their transcripts, and cDNA. Note that the term "nucleic acid" herein includes a polynucleotide including desired simple nucleotides and/or modified nucleotides, examples of which encompass cDNA, mRNA, total RNA, and hnRNA. The term "modified nucleotides" encompasses: phosphate esters such as inosine, acetylcytidine, methylcytidine, methyladenosine, and methylguanosine; and nucleotides that can be acquired by an effect of ultraviolet rays or chemical substances.

The term "nucleotide sequence" is used interchangeably with "nucleic acid sequence", and is presented as a sequence of deoxyribonucleotides (each abbreviated as A, G, C, or T). Further, a polynucleotide or a "nucleotide sequence" of a polynucleotide is intended to mean (i) a sequence of deoxyribonucleotides for a DNA molecule or a polynucleotide and (ii) a sequence of ribonucleotides (A, G, C, and U) (each thymidine (T), which is a deoxynucleotide, in the deoxynucleotide sequence specified herein is replaced with uridine (U), which is a ribonucleotide) for an RNA molecule or a polynucleotide.

For example, an RNA molecule having the sequence shown in SEQ ID NO: 2 or 4, which is represented by abbreviations for deoxyribonucleotides, is intended to mean an RNA molecule having a sequence in which deoxynucleotides A, G, and C shown in SEQ ID NO: 2 or 4 are substituted with their corresponding ribonucleotides A, G, and C and deoxynucleotide T shown in SEQ ID NO: 2 or 4 is substituted with ribonucleotide U. Further, a polynucleotide having the nucleotide sequence shown in SEQ ID NO: 2 or 4 or a fragment of the polynucleotide is intended to mean a polynucleotide having a sequence represented by deoxynucleotides A, G, C and/or T shown in SEQ ID NO: 2 or 4 or a fragment of the polynucleotide.

A fragment (partial sequence) of the gene of the present invention may be used as a primer for polymerase chain reaction (PCR) or as a hybridization probe. The fragment (polynucleotide) is available in specific PCR amplification of a homologue or an orthologue of the gene of the present invention, and is also available as a hybridization probe which specifically hybridizes with a homologue or an ortho- logue of the gene of the present invention. That is, in a preferable embodiment, the fragment of the gene of the present invention is useful for diagnosis (i) as a primer for amplification of a target sequence performed by means of polymerase chain reaction (PCR) or (ii) as a probe according to a conventional DNA hybridization technique.

Further, other examples for use of the fragment of the gene of the present invention encompass: in situ hybridization (e.g., FISH) with respect to a mitotic chromosome spread, by which in situ hybridization a correct chromosome site is shown (described in Verma et al., Human Chromosomes: a Manual of Basic Techniques, Pergamon Press, New York (1988)); and northern blotting analysis for detection of mRNA of the present invention expressed in a certain tissue.

Examples of the gene of the present invention encompass, but are not limited to: a polynucleotide by itself encoding an amino acid sequence of a maturation protein; a coding sequence of a maturation protein and its further sequence (e.g., a sequence encoding a leader sequence) (e.g., a preprotein sequence, a proprotein sequence or a preproprotein sequence); intron, a non-coding 5' sequence and a non-coding 3' sequence (e.g., a transcription untranslated region working in transcription and mRNA processing (including splicing and a polyadenylated signal)); and a further coding sequence encoding another amino acid providing further functionality.

Therefore, for example, a sequence encoding a protein may be fused to a marker sequence (e.g., a sequence encoding a peptide which facilitates purification of a fused protein). In a preferable embodiment of the present invention, a marker amino acid sequence may be a hexa-histidine peptide, such as a tag provided in pQE vector (Qiagen, Inc.). As described in "Gentz et al., Proc. Natl. Acad. Sci. USA 86: 821-824 (1989)", the hexa-histidine peptide is useful in purifying a fusion protein in a simple manner. Alternatively, a publicly and/or commercially available marker amino acid sequence of many kinds can be used. For example, as described in "Wilson et al., Cell 37: 767 (1984)", an "HA" tag is another peptide useful in purification, which HA tag corresponds to an epitope derived from an influenza hemagglutini (HA) protein. Further alternatively, a fusion protein made by causing the Fc to be fused with the N-terminal or the C-terminal of the protein of the present invention would be useful for purification.

Further, the present invention encompasses a mutant of the gene of the present invention. The mutant can naturally occur as well as a natural allele mutant does. The "allele mutant" is intended to mean one of some interchangeable forms of a gene occupying a predetermined gene locus on a chromosome of an organism. Further, a non-naturally-occurring mutant may be produced by using e.g., a mutagenesis technique known in the art. Examples of such the mutant encompass a mutant produced by a substitution, deletion, or addition of one or several nucleotides, as described above. The substitution, deletion, or addition may occur at one or more nucleotides. The mutant may include mutation occurred in a coding region, a non-coding region or both of them. Mutation in a coding region may cause a conservative or nonconservative substitution, deletion, or addition of an amino acid.

In addition to the maturation protein, examples of a preferable protein of the present invention encompass: an extracellular domain, a transmembrane domain, an intracellular domain, and a protein which lacks the whole of or part of a transmembrane domain but includes extracellular and intracellular domains. The term "protein" herein is interchangeably used with "polypeptide" or "peptide". Further, the present invention provides a polypeptide with a substitution, addition, and/or deletion of one or several amino acids of a protein encoded by the nucleotide sequence shown in SEQ ID NO: 2. A conservative or nonconservative substitution, deletion, and/or addition of an amino acid(s) is/are preferable, and a silent substitution, addition, and/or deletion thereof is/are particularly preferable. These do not change characteristics and activity of the protein of the present invention or part of the protein. In terms of this point, particularly preferable one is a conservative substitution.

Further, the protein of the present invention may be not only the one isolated from natural sources but also the one chemically synthesized or obtained by recombination. That is, the protein of the present invention may be isolated and purified from e.g., cells or tissues. Alternatively, the protein of the present invention may be expressed intracellularly by being encoded by a gene that has been transferred into the host cell. Further, the protein of the present invention may include an additional polypeptide.

The present invention relates to a polypeptide having an amino acid sequence of an epitope-bearing part of the protein described herein. The polypeptide having the amino acid sequence of the epitope-bearing part of the protein of the present invention only needs to include part of a polypeptide which part includes at least 6, 7, 8, 9 or 10 amino acids. In addition, such the polypeptide may also be an epitope-bearing-part polypeptide having a length (optionally set) equal to or shorter than a length of an entire amino acid sequence of (i) a protein encoded by the nucleotide sequence shown in SEQ ID NO: 2 or 4 or (ii) a protein having the amino acid sequence shown in SEQ ID NO: 1.

In other words, the present invention provides an epitope-bearing peptide of the protein of the present invention. As described in the later-described Example, the protein of the present invention is immunogenic. Therefore, it is possible to identify, in the protein of the present invention, an epitope part inducing an antibody response, according to a method known in the art. For example, Geysen, H. M. et al., Proc. Natl. Acad. Sci. USA 81: 3998-4002 (1984) discloses a procedure of a rapid concurrent synthesis on solid supports of hundreds of peptides having sufficient purity to react in an enzyme-linked immunosorbent assay. Interaction of synthesized peptides with antibodies is then easily detected without removing them from the supports. In this manner, a peptide bearing an immunogenic epitope of a desired protein may be identified routinely by a person skilled in the art. For example, an immunologically important epitope in a coat protein of foot-and-mouth disease virus was located by Geysen et al. with the resolution of seven amino acids by the synthesis of an overlapping set of all 208 possible hexapeptides covering an entire 213 amino acid sequence of a protein. Then, a complete replacement set of peptides in which all 20 amino acids were substituted in turn at every position within the epitope was synthesized, and particular amino acids conferring specificity for a reaction with an antibody were determined. Thus, a peptide analog of the epitope-bearing peptide of the present invention can be made routinely by this method. U.S. Pat. No. 4,708,781, Geysen (1987) describes further details of this method by which a peptide bearing an immunogenic epitope of a desired protein is identified.

The "immunogenic epitope" is defined as part of a protein which part induces an antibody response, in a case where the whole of the protein is an immunogen. The immunogenic epitopes are considered to be limited to two or more regions on a molecule. On the other hand, a site of a protein molecule to which site an antibody can bind is defined as "antigenic epitope". Generally, in a protein, the number of immunogenic epitopes is less than that of antigenic epitopes. For example, see Geysen, H. M. et al., Proc. Natl. Acad. Sci. USA 81: 3998-4002 (1984).

An antigenic epitope-bearing peptide of the present invention is useful for induction of antibodies including a monoclonal antibody which specifically binds to the protein of the present invention. Therefore, most of hybridomas obtained by fusion of spleen cells taken from a donor immunized with the antigenic epitope-bearing peptide secretes antibodies generally reactive with natural proteins. The antibodies induced by the antigenic epitope-bearing peptide are useful to detect mimicked proteins, and antibodies against different peptides may be used for tracking the fate of various regions of a protein precursor which undergo post-translational processing. A peptide and an anti-peptide antibody may be used in a variety of qualitative or quantitative assays for the mimicked proteins (e.g., in competition assays), since it has been shown that, in immunoprecipitation assays, even short peptides (e.g., approximately 9 amino acids) can bind and substitute longer peptides. For example, see Wilson, I. A. et al., Cell 37: 767-778 (1984) 777. An anti-protein antibody of the present invention is also useful for purification of the mimicked proteins (e.g., by adsorption chromatography using a method known in the art).

The antigenic epitope-bearing peptide of the present invention designed according to the above guideline preferably includes a sequence of at least seven, more preferably of at least nine, most preferably between approximately 15 to approximately 30 amino acids included in the amino acid sequence of the protein of the present invention. However, a peptide or a polypeptide including a larger portion of the amino acid sequence of the protein of the present invention, containing approximately 30 to approximately 50 amino acids, or any length up to and including the entire amino acid sequence of the protein of the present invention, also are considered the epitope-bearing peptide of the present invention, and also are useful for inducing antibodies that react with a mimicked protein. Preferably, an amino acid sequence of the epitope-bearing peptide is selected so that it can provide a substantial solubility in an aqueous solvent (i.e., the selected sequence contains a relatively hydrophilic residue, and a highly-hydrophobic sequence is preferably avoided); and a sequence containing a proline residue is particularly preferable.

The epitope-bearing peptide of the present invention may be produced by desired, conventional recombinant protein producing means which uses the gene of the present invention. For example, a short epitope-bearing amino acid sequence may be fused with a larger polypeptide which acts as a carrier, during production and purification of a recombinant and immunization for producing an anti-protein antibody. The epitope-bearing peptide may also be synthesized by using a known method for a chemical synthesis.

Further, the present invention may encompass a protein to be expressed into which protein an appropriate secretory signal has been incorporated, for secretion of a translated protein to the inside of a lumen of an endoplasmic reticulum, to the inside of a periplasm space, or to an extracellular environment. The secretion signal may be endogenous with respect to a polypeptide, or may be a heterogenous signal.

Therefore, the protein of the present invention can be expressed in a modified form such as a fusion protein, and may include not only the secretion signal but also an additional heterogenous functional region. For example, an additional amino acid, particularly, a region of an electrically charged amino acid can be added to the N-terminal of a protein for improvement in stability and durability in the host cells during purification or subsequent manipulation and storage. Further, a peptide portion can be added to a protein for facilitating purification. Such a region can be removed before a final preparation of the protein. In particular, addition of a peptide portion to a protein for the purpose of causing secretion or excretion, improving stability, and facilitating purification is well known in the art, and is a technique routinely performed.

A preferable fusion protein includes a heterogeneous region derived from immunoglobulin which heterogeneous region is useful for making a protein soluble. For example, EP A 0 464 533 (Canadian counterpart application 2045869) discloses fusion proteins including various portions of constant regions of immunoglobulin molecules together with another human protein or part thereof. In many cases, employing the Fc region of a fusion protein is sufficiently advantageous for use in therapy and diagnosis, thereby resulting in, for example, improved pharmacokinetic properties (EP A 0232 262). On the other hand, for some uses, it is desirable that the Fc part is deleted after the fusion protein has been expressed, detected, and purified in an advantageous manner described. This is a case where the Fc portion proves to be a hindrance to use in therapy and diagnosis (e.g., in a case where the fusion protein is to be used as an antigen for immunizations). In drug screening, for example, human proteins such as hIL-5 have been fused with Fc portions for use in a high-throughput screening assay to identify an antagonist of hIL-5. See D. Bennett et al., Journal of Molecular Recognition Vol. 8: 52-58 (1995), and K. Johanson et al., The Journal of Biological Chemistry Vol. 270, No. 16, pages 9459-9471 (1995).

(1-2) Functions

The following describes detailed functions of the protein of the present invention, taking above-described protein SITH-1 as an example.

As shown in the later-described Example, an SITH-1 gene was expressed at all times in the cytoplasm of cells latently infected with HHV-6, but not in productively infected cells. The gene encoding the protein SITH-1 is encoded by DNA which forms a complementary strand to the previously reported HHV-6 latent infection specific gene (H6LT), and expression of the gene is enhanced at the intermediate stage of latent infection with HHV-6.

From these facts, the protein SITH-1 is considered to be a protein that is expressed specifically during latent infection with HHV-6. Further, the protein SITH-1 has been found to be clearly different from the heretofore-identified proteins that are involved in latent infection with HHV-6.

Further, the present inventors proceeded functional analysis of the protein SITH-1, and found the following fact: the protein SITH-1 binds to CAML (calcium-modulating cyclophilin ligand, Accession #; U18242), which is a host protein, so as to increase a calcium concentration in glial cells such as astrocytes. CAML is a protein that occurs abundantly within a brain and lymphocytes in a host's living body, and is known to increase a calcium concentration in cells. In addition, the increase in the intracellular calcium concentration due to the expression of the protein SITH-1 is considered to induce activation of general signal transduction within the latently infected cell, thereby contributing to efficient reactivation of HHV-6.

By the term "glial cells" as used herein are meant all kinds of glial cells including mature and precursor forms of glial cells in a central nervous system, as exemplified by astrocytes, oligodendrocytes, microglias, and ependymal cells. Other types that may be encompassed are satellite cells, Schwann cells, and terminal gliocytes in a peripheral nervous system.

HHV-6 is known to cause latent infection of glial cells (e.g., astrocytes) in a brain. It is believed that the calcium concentration in glial cells (e.g., astrocytes) rises, if HHV-6 being at a stage of latent infection or an intermediate stage, which is a latent infection state characterized by high activity, causes SITH-1 to be expressed. As a result of findings recently made in the mental science fields, an increase of the intracellular calcium concentration within brain cells is considered to be closely related to mood disorders and other mental disorders.

In fact, as shown in the Example, expressing the protein SITH-1 in mouse glial cells (e.g., astrocytes) turned out to induce symptoms similar to those of mood disorders, which are mental disorders, and to increase sensitivity. This strongly suggests the possibility that HHV-6 latently infecting glial cells (e.g., astrocytes) can trigger a mental disorder via the protein SITH-1.

Furthermore, HHV-6 can infect not only astrocytes but also other types of glial cells such as microglia. Therefore, mental disorders such as depression and manic-depressive illness may be caused by other types of glial cells in addition to astrocytes.

The above findings show that the protein of the present invention has ability to retain activity for binding to CAML, which is a host protein, and for increasing the intracellular calcium concentration. It has also been found that a mental disorder can be induced by causing the protein of the present invention to be expressed in glial cells (e.g., astrocytes) where the strongest expression of this protein is likely to occur. Thus, the protein of the present invention is considered to have ability to cause a mental disorder in the host by being expressed during latent infection with the herpes virus or at an early stage of its reactivation.

(1-3) Methods for Obtaining Gene and Protein

Methods for obtaining (or producing) the gene and the protein of the present invention are not specifically limited. The following describes typical examples of the methods.

<Method for Obtaining Protein>

As described above, the method for obtaining the protein of the present invention (or the method for producing the protein) is not particularly limited. Examples of the method encompass a method for simple purification from biological samples (e.g., cells, tissues, or an individual organism) containing the protein of the present invention. Also, the method for purification is not particularly limited, and may be performed in such a manner that an extract solution is extracted from cells or tissues by a known method, and the extract solution is then purified by a known method (e.g., a method using a column). For example, the protein of the present invention can be purified and isolated by performing a high performance liquid chromatography (HPLC) with respect to a crude protein fraction extracted from cells or tissues.

Further, other examples for the method for obtaining the protein of the present invention encompass a method using e.g., a gene recombination technique. In this case, for example, the following method can be adopted: The gene of the present invention is incorporated into e.g., a vector, the vector is then transferred into a host cell by a known method so as to be capable of being expressed therein, and the protein obtained by translation within the cell is purified. Specific methods for transfer of the gene (transformation), the expression of the gene, and the like will be described later.

Note that, for transfer of a foreign gene into a host as above, a vector and a host may be selected depending on its purpose, since there are various kinds of hosts and expression vectors including a promoter which functions in the host for expression of the foreign gene. The method for purifying a produced protein differs depending on the host used and/or the characteristics of the protein. However, use of a tag allows a target protein to be purified in a relatively easy manner, for example.

A method for producing the mutant protein is also not limited to any specific one. A known mutant protein producing method can be used, for example, site-directed mutagenesis (Hashimoto-Gotoh, Gene 152, 271-275 (1995), and others), a method for producing a mutant protein by introducing point mutation into a nucleotide sequence through the PCR technique, or a method for producing a mutant line by insertion of transposon. By using any of these methods, it is possible to produce the mutant protein by causing, in a nucleotide sequence of cDNA encoding the protein (a), a mutation of a substitution, deletion, insertion, and/or addition of one or several nucleotide. Further, the mutant protein may be produced by using a commercially-available kit.

The method for obtaining the protein of the present invention is not limited to the above ones. Alternatively, for example, a chemical synthesis using e.g., a commercially-available peptide synthesizer may be used. Further alternatively, for example, a cell-free protein synthesis solution may be used for synthesizing the peptide of the present invention from the gene of the present invention.

<Method for Obtaining Gene>

As described above, the method for obtaining the gene of the present invention (or the method for producing the gene) is also not particularly limited, and may be, for example, a method using a differential screening (subtraction cloning). This method may be performed in such a manner that, according to a known technique, direct hybridization is repeatedly performed in a test tube so as to condense target cDNA (the gene of the present invention).

Each step in the differential screening may be performed under conditions conventionally applied. As for a clone obtained as a result of this, a restriction enzyme map may be created, and a nucleotide sequence (sequencing) may be determined, for more detailed analysis of the clone. This analysis makes it possible to easily confirm whether or not a DNA fragment including the sequence of the gene of the present invention is obtained.

Alternatively, the method for obtaining the gene of the present invention may be a method for isolating and cloning, according to a known method, a DNA fragment including the gene of the present invention. For example, a probe which specifically hybridizes with part of the sequence of the cDNA may be prepared, and screening of a genomic DNA library or a cDNA library may be performed. The probe may have any sequence and/or length, as long as it specifically hybridizes with at least part of the sequence of the cDNA or its complementary sequence.

Further alternatively, the method for obtaining the gene of the present invention may be a method using amplification means such as PCR. For example, primers are respectively prepared based on the 5' and 3' ends of a cDNA sequence (or its complementary sequence) of the gene of the present invention, and the primers are used to perform e.g., PCR with a genomic DNA (or cDNA) as a template, so that a DNA region between the primers is amplified. In this way, DNA fragments including the gene of the present invention can be obtained in mass quantity.

Still alternatively, a polynucleotide having the sequence may be synthesized by a known chemical synthesis, based on gene sequence information.

(2) Antibody of the Present Invention

The antibody of the present invention is obtained as a polyclonal or monoclonal antibody by a known method using, as an antigen, the protein of the present invention (e.g., the protein (a) or (b)) or a partial peptide thereof. Examples of the known method include those that are described in documents such as: Harlow et al., "Antibodies: A laboratory manual (Cold Spring Harbor Laboratory, New York (1988); and Iwasaki et al., "*Tankurohn koutai haiburidoma to ELISA* (Monoclonal Antibody Hybridomas and ELISA)", Kodansha (1991)). The antibody thus obtained may be utilized in detecting and assaying the protein of the present invention.

For example, the epitope-bearing peptide of the present invention described in the above (1-1) is used to induce an antibody by a method known in the art. For example, see: Chow, M. et al., Proc. Natl. Acad. Sci. USA 82: 910-914; and Bittle, F. J. et al., J. Gen. Virol. 66: 2347-2354 (1985). Generally, animals can be immunized with a free peptide; however, an anti-protein antibody titer can be increased by booster immunization by coupling of a peptide to a high-molecular carrier (e.g., keyhole limpet hemocyanin (KLH) or tetanus toxoid). For example, a peptide containing cysteine can be coupled to a carrier with use of a linker such as m-maleimidobenzoyl-N-hydroxysuccinimide ester (MBS), whereas other peptides can be coupled to carriers with use of more general linkers such as glutaraldehyde. Animals such as rabbits, rats, and mice are immunized with a free or a carrier-coupling peptide, for example, by intraperitoneal and/or intradermic injection of approximately 100 µg of an emulsion including a peptide or a carrier protein and Freund's adjuvant. Some booster immunization injections may be required e.g., at 2-week intervals, for example, for providing an anti-protein antibody having a useful titer which is detectable in an ELISA assay using a free peptide adsorbed to a surface of a solid. An anti-protein antibody titer in the serum from an immunized animal can be increased by selection of an anti-protein antibody, e.g., by adsorption to a peptide on a solid support by a method known in the art and by dissolution of the selected antibody.

The term "antibody" herein means immunoglobulins (IgA, IgD, IgE, IgG, IgM and their Fab fragments, $F(ab')_2$ fragments, and Fc fragments); examples of which include, but are not limited to, polyclonal antibodies, monoclonal antibodies, single-chain antibodies, anti-idiotype antibodies, and humanized antibodies.

The term "antibody that recognizes a protein of the present invention" herein is intended to encompass complete molecules and antibody fragments (e.g., Fab and $F(ab')_2$ fragments) that are capable of specifically binding to the above-described protein of the present invention. The Fab and $F(ab')_2$ fragments, each of which lacks an Fc fragment included in an intact antibody, are cleared more rapidly from circulation, and may hardly have specific tissue binding of the intact antibody (Wahl et al., J. Nucl. Med. 24: 316-325 (1983)). For this reason, these fragments are preferable.

Further, another antibody capable of recognizing the protein of the present invention may be produced by a two-step procedure through use of an anti-idiotype antibody. This method takes advantage of the fact that an antibody itself is an antigen; therefore this method is capable of giving an antibody binding to a second antibody. According to this method, an antibody specific to the protein of the present invention is used to immunize animals (preferably, mice). Subsequently, spleen cells of the animals are used to produce hybridoma cells, which are then subjected to screening for identifying a clone producing an antibody whose ability to bind to the antibody specific to the protein of the present invention can be blocked by a protein antigen of the present invention. Such the antibody may be an anti-idiotype antibody against the antibody specific to the protein of the present invention, and may be used to immunize animals for inducing formation of further antibodies specific to the protein of the present invention.

It is clear that the Fab fragment, the $F(ab')_2$ fragment, and other fragments of the antibody of the present invention may be used according to the methods disclosed herein. These fragments are produced by cleavage caused by proteolysis using an enzyme, typical examples of which encompass papain (giving an Fab fragment) or pepsin (giving an $F(ab')_2$ fragment). Alternatively, a protein-binding fragment of the present invention can be produced by application of a recombinant DNA technique or through synthetic chemistry.

In detection of an increased level of the protein of the present invention using in vivo imaging for the purpose of diagnosis on humans, it can be preferable to use a "humanized" chimeric monoclonal antibody. Such the antibody can be generated using a genetic construct derived from hybridoma cells that generate the above-mentioned monoclonal antibody. Methods for generating chimeric antibodies are known in the art of interest. For general descriptions thereof, see: Morrison, Science 229: 1202 (1985); Oi et al., BioTechniques 4: 214 (1986); Cabilly et al. U.S. Pat. No. 4,816,567; Taniguchi et al., EP 171496; Morrison et al., EP 173494; Neuberger et al., WO 8601533; Robinson et al., WO 8702671; Boulianne et al., Nature 312: 643 (1984); and Neuberger et al., Nature 314: 268 (1985).

(3) Recombinant Expression Vector of the Present Invention

The recombinant expression vector of the present invention includes the gene of the present invention encoding the protein (a) or (b). The recombinant expression vector may be, for example, a recombinant expression vector into which cDNA has been inserted. The recombinant expression vector may be produced by using e.g., a plasmid, a phage, or a cosmid (not limited to these). Further, a production method of the recombinant expression vector may employ a known method.

The vector is not limited to any specific kind, and may be any one as long as it is capable of being expressed in a host cell (host). That is, the expression vector may be one prepared as follows: In order that a gene is surely expressed, a promoter sequence is selected as needed according to the type of the host cell; and the promoter sequence thus selected and the gene of the present invention are incorporated into e.g., a plasmid of various kinds. Examples of the expression vector encompass: phage vectors; plasmid vectors; virus vectors; retrovirus vectors; chromosome vectors; episome vectors; and virus-derived vectors (for example, vectors derived from bacterial plasmids, bacteriophages, yeast episomes, yeast chromosome elements, viruses (e.g., baculoviruses, papovaviruses, vaccinia viruses, adenoviruses, avipoxviruses, pseudorabies viruses, herpesviruses, lentiviruses, and retroviruses), and combinations thereof, e.g., cosmids and phagemids).

Generally, introduction of the plasmid vector is performed in sediments such as calcium phosphate sediments or in a complex with charged lipids. In a case where the vector is a virus, the vector can be packaged in vitro using an appropriate packaging cell line, and can subsequently be transduced into a host cell. The retrovirus vector may be replicable or replication-defective. In the latter case, propagation of the virus generally occurs only in a complementary host cell.

Further, vectors each including a cis-acting regulating region for a target gene are preferable. An appropriate trans-acting factor may be supplied by a host, by a complementary vector, or by the vector itself during introduction of the vector into the host. In a preferable embodiment in this regard, vectors each providing specific expression which may be inducible and/or cell-type specific are preferable. Particularly preferred among such vectors are those inducible by environmental factors that are easy to manipulate, such as temperature and nutritional additives.

Examples of a preferable bacteria vector to be used encompass: pQE70, pQE60, and pQE-9 (available from Qiagen); pBS vector, Phagescript vector, Bluescript vector, pNH8A, pNH16a, pNH18A, pNH46A (available from Stratagene); and ptrc99a, pKK223-3, pKK233-3, pDR540, pRIT5 (available from Phrmacia). Further, examples of a preferable eukaryote vector encompass pWLNEO, pSV2CAT, pOG44, pXT1, and pSG (available from Stratagene); and pSVK3, pBPV, pMSG, and pSVL (available from Phrmacia).

Various kinds of markers may be used to confirm whether or not the gene of the present invention has been transferred into the host cell, and to confirm whether or not the gene is surely expressed in the host cell. That is, the expression vector preferably includes at least one selection marker. Examples of such a selection marker encompass: dihydrofolic acid reductase or neomycin resistance for eukaryote cell culture; and drug resistance genes such as a tetracycline-resistant gene and an ampicillin-resistance gene for culture of E. coli and other bacteria. Another example uses, as a marker, a gene deleted in a host cell, and introduces, as an expression vector, a plasmid or the like including the marker and the gene of the present invention into the host cell. From expression of the marker gene, it is possible to confirm that the gene of the present invention has been transferred. Alternatively, the protein of the present invention may be expressed as a fusion protein. For example, with Green Fluorescent Protein (GFP) derived from Aequorea victoria used as a marker, the protein of the present invention may be expressed as a GFP fusion protein. Further, the gene of the present invention may be bound to a vector including a selection marker for propagation in the host cell.

Further, it is preferable that a DNA insert is operably linked to an appropriate promoter (e.g., phage λPL promoter, E. coli lac promoter, trp promoter, tac promoter, SV40 early promoter and late promoter, and a promoter of retrovirus LTR). As another appropriate promoter, any one known to a person skilled in the art may be used.

In the present invention, known bacteria promoters which are preferably used encompass E. coli lad and lacZ promoters, T3 promoter and T7 promoter, gpt promoter, λPR promoter and λPL promoter, and trp promoter. Suitable eukaryote promoters encompass CMV immediate-early promoter, HSV thymidine kinase promoter, early SV40 promoter and late SV40 promoter, a promoter of retrovirus LTR (e.g., a promoter of Rous sarcoma virus (RSV)), and metallothionein promoter (e.g., mouse metallothionein I promoter).

It is preferable that the recombinant expression vector further includes: sites for transcription start and transcription termination; and a transcription region containing a ribosome-binding site for translation. A matured transcript expressed by a vector construct includes a coding region containing (i) transcription start AUG at the start of a polypeptide to be translated and (ii) a stop codon which is properly positioned at the end of the polypeptide.

Transcription of DNA by a higher eukaryote may be enhanced by insertion of an enhancer sequence into a vector. The enhancer is a DNA cis-acting element (generally, approximately 10 bp to 300 bp) which works for enhancing transcriptional activity of a promoter of a predetermined host cell type. Examples of the enhancer encompass: SV40 enhancer (positioned at 100 bp to 270 bp on the late side of a replication origin); an early promoter enhancer of a cytomegalovirus; a polyoma enhancer on the late side of a replication origin; and an adenovirus enhancer.

The above host cell is not limited to any specific one, and a conventionally-known cell of various kinds may suitably be used. Typical examples of an appropriate host encompass: bacterial cells (e.g., E. coli cells, Streptomyces cells, and Salmonella typhimurium cells); fungus cells (e.g., yeast cells); insect cells (e.g., Drosophila S2 cells and Spodoptera Sf9 cells); animal cells (e.g., CHO cells, COS cells, and Bowes melanoma cells); and plant cells. More specific examples thereof encompass not only mammal cells such as human cells and mouse cells but also cells derived from Bombys mori, insects such as Drosophia melanogaster, bacteria such as E. coli (Escherichia coli), yeasts (Saccharomyces cerevisiae and Schizosaccharomyces pombe), and Caenorhabditis elegans, and oocyte cells of Xenopus laevis. However, the present invention is not limited to these. A culture medium and conditions suitable for each of the above host cells may be ones known in the art.

A method for introducing the expression vector into the host cell, i.e., a method for transformation is also not limited to any specific one, and a conventionally-known method may suitably be used, for example, electroporation, a calcium phosphate method, a liposome method, a DEAE dextran method, microinjection, cationic lipid-mediated transfection, electroporation, transduction, or infection. These methods are described in many standard laboratory manuals, for example, Davis et al., Basic Methods In Molecular Biology (1986).

Note that the present invention can also provide (i) a recombinant expression vector including a polynucleotide encoding a partial fragment of the protein of the present invention and (ii) a transformant (host cell) genetically modified by the recombinant expression vector, each of which is for recombinantly producing a partial fragment (fragment) of the protein of the present invention.

Further, the present invention may also encompass an invention related to production of the protein of the present invention or a fragment thereof by means of the above recombinant techniques. That is, the present invention may also encompass a method for producing the protein of the present invention and its fragment through use of a recombinant technique. A recombinant protein produced by the technique may be collected and purified from a recombinant cell culture product by means of a known method, e.g., an ammonium sulfate precipitation or ethanol precipitation, acid extraction, anion- or cation-exchange chromatography, phosphocellulose chromatography, hydrophobic interaction chromatography, affinity chromatography, hydroxyapatite chromatography, or lectin chromatography. Most preferable one used for purification is high-performance liquid chromatography ("HPLC").

(4) Transformant of the Present Invention

The transformant of the present invention is a transformant into which the gene of the present invention has been transferred, i.e., a transformant into which the recombinant expression vector described in the above (3) has been transferred. The expression "gene has been transferred" herein means that the gene has been transferred into a target cell (host cell) in an expressible manner by means of a known gene engineering method (genetic manipulation technique). Further, the "transformant" means not only a cell, a tissue, and an organ but also an individual organism.

A method for preparing (producing) the transformant of the present invention may be, for example, a method for transforming the above recombinant expression vector. An organism to be transformed is also not limited to any specific one, examples of which encompass various kinds of microorganisms and animals (e.g., a transgenic mouse) exemplified in the above descriptions concerning the host cell. Further, with a promoter and/or a vector selected, a plant can also be a subject to be transformed.

(5) Gene Detection Instrument of the Present Invention

A gene detection instrument of the present invention uses, as a probe, at least part of a nucleotide sequence, or its complementary sequence, of the gene of the present invention. The gene detection instrument can be used to e.g., detect and/or measure an expression pattern of the gene of the present invention under various conditions.

The gene detection instrument of the present invention may be, for example, a DNA chip including a substrate (support) on which the probe specifically hybridizing the gene of the present invention is immobilized. The "DNA chip" herein primarily refers to a synthetic DNA chip which uses, as the probe, a synthesized oligonucleotide. Not only that, the term "DNA chip" herein also encompasses an attachment-type DNA microarray which uses, as the probe, cDNA such as a PCR product.

A sequence used as the probe may be determined by a conventionally-known method for determining a characteristic sequence from a cDNA sequence. Specifically, for example, the method may be a Serial Analysis of Gene Expression (SAGE) method (Science 276:1268, 1997; Cell 88:243, 1997; Science 270:484, 1995; Nature 389:300, 1997; U.S. Pat. No. 5,695,937).

Note that the DNA chip may be manufactured by a known method. For example, in order to use a synthesized oligonucleotide as the oligonucleotide, a photolithography technique and a solid-phase DNA synthesis technique may be used in combination so that the oligonucleotide is yielded through synthesis on a substrate. On the other hand, in order to use cDNA as the oligonucleotide, the cDNA may be attached on a substrate with an arrayer.

Further, as well as in conventional DNA chips, a detection accuracy for a gene may be further enhanced by providing a perfect-match probe (oligonucleotide) together with a mismatch probe, which differs from the perfect-match probe by a single base substitution. Further, in order to detect different genes in parallel, a DNA chip may be configured such that a plurality of kinds of oligonucleotides are immobilized on a single substrate.

The following describes the gene detection instrument of the present invention in greater detail.

<Substrate>

A material of the substrate for use in the gene detection instrument of the present invention only needs to be one on which an oligonucleotide can stably be immobilized. Examples of the material encompass, but are not limited to, synthetic resins (e.g., polycarbonate and plastic) and glass. A shape of the substrate is also not limited to any specific one. For example, a plate-shaped substrate or a film-shaped substrate may preferably be used.

<Oligonucleotide to be Immobilized on Surface of Substrate>

The oligonucleotide to be immobilized on the surface of the substrate of the gene detection instrument of the present invention only needs to be an oligonucleotide which is based on at least part of the nucleotide sequence of the gene of the present invention. By establishment of hybridization between the oligonucleotide and a nucleic acid derived from a sample, it is possible to detect a gene contained in the sample. Note that the oligonucleotide which is based on at least part of the nucleotide sequence of the gene of the present invention will be hereinafter referred to as "capture oligo" in some cases.

The capture oligo may be designed based on the nucleotide sequence of the gene of the present invention. Thus, the capture oligo may be the nucleotide sequence itself, or may include a mutation as long as it allows establishment of specific hybridization between the capture oligo and a nucleic acid prepared from a sample to be detected. The position of the mutation is not particularly limited.

A length (the number of bases) of the capture oligo is not particularly limited. However, if the length is too short, detection of the hybridization becomes difficult; if the length is too long, non-specific hybridization is allowed. The present inventors kept studying optimization of the length of the capture oligo, and determined 12 to 50 base length as a standard length. The standard length is preferably 12 to 40 base length, more preferably 12 to 30 base length, further preferably 13 to 22 base length. However, the present invention is not limited to this. The base length depends primarily on sequence characteristics (a content of a certain base, repetition of a certain base). Further, the present inventors have confirmed that even a short-chained capture oligo is capable of specific hybridization provided that the short-chained capture oligo has a fine binding.

In a case where the capture oligo has any of a hair-pin structure, a loop structure, and other tertiary structures each of which hinders hybridization with a nucleic acid derived from a sample, substituting one or more nucleotides constituting the capture oligo with inosine or a nucleic acid(s) not paired with any nucleotide(s) can cancel the tertiary structure.

A synthesis method of the capture oligo is not limited to any specific one. For example, a known method (e.g., the method described in Maniatis, T. et al., Molecular Cloning A Laboratory Manual, Second Edition, Cold Spring Harbor Laboratory Press (1989)) may be used. Generally, the capture oligo can be chemically synthesized with use of a commercially-available DNA synthesizer.

In the gene detection instrument of the present invention, it is preferable that a so-called control capture oligo as well as the oligonucleotide which is based on at least part of the nucleotide sequence of the gene of the present invention are immobilized on the surface of the substrate. The control capture oligo includes a positive control capture oligo and a negative control capture oligo. The positive control capture oligo is used to check whether or not an amplification reaction is successfully proceeding in the later-described probe preparing step. The negative control capture oligo is used to check for non-specific hybridization, i.e., a false-positive hybridization signal. The present invention also encompass a gene detection instrument in which these positive control capture oligo and negative control capture oligo are immobilized on the surface of the substrate.

The positive control capture oligo may be any oligonucleotide, as long as it is designed based on a nucleotide sequence included in a probe prepared from a sample to be detected. Further, in order that a plurality of samples to be detected are detected at once with use of a single gene detection instrument, positive control capture oligos may be designed respectively for the samples to be detected, or a positive control capture oligo may be designed based on a nucleotide sequence shared by probes prepared from the plurality of samples to be detected. In case there is no nucleotide sequence shared by the probes prepared from all of the samples to be detected, a positive control capture oligo may be designed for each of some groups. Alternatively, an artificial sequence may be designed so that it has a different sequence from a sequence of a subject bacterium but has a common primer sequence, and a part of the artificial sequence may be used as a positive control capture oligo. With such an artificial sequence used as a template, a probe can be prepared (such a probe is herein called "control probe"), and the resulting probe is added to a probe prepared from a sample. In this way, specificity of the hybridization can be tested. More details on the probe will be discussed below.

It is preferable that the negative control capture oligo is designed such that it has a nucleotide sequence of a positive control capture oligo with an artificial substitution of one or more bases but less than 20% of the total bases of the sequence. The number of substituted bases is determined taking into consideration of hybridization conditions so that the negative control capture oligo does not hybridize with the probe derived from the sample to be detected.

The sample to be detected is not limited to any specific one. Further, the number of kinds of capture oligos to be immobilized on one substrate only needs to be one or more, and there is no upper limit for it. Also, it is most preferable that the gene detection instrument of the present invention is designed to be a so-called microarray type in which a plurality of partial fragments (having different nucleotide sequences) of the gene of the present invention are immobilized on one substrate as capture oligos.

<Immobilization of Oligonucleotide (Capture Oligo)>

A method for immobilizing the oligonucleotide on the surface of the substrate is not limited to any specific one, but may be selected from known methods as needed. For example, means used for general hybridization methods, e.g., physical adsorption, electrical bonding, or molecular covalent bonding, is available. For the gene detection instrument of the present invention, it is preferable to use a substrate having a carbodiimide group or an isocyanate group on its surface (U.S. Pat. No. 5,908,746, Tokukaihei, No. 8-23975) for immobilization.

If an amount of the oligonucleotide spotted on the substrate is too small, detection may be difficult because there may not be enough reaction between the oligonucleotide and the probe. Further, high-integration spotting brings about technical problems and a high cost, and also requires an expensive higher-precision detection instrument (e.g., a scanner) for detecting a hybridization signal by using e.g., a fluorescent label of the probe or chemiluminescence. Therefore, it is preferable to immobilize, on the surface of the substrate, the oligonucleotide within a size of 10 µm to 1,000 µm in diameter. A method for spotting the oligonucleotide onto the substrate is not limited to any specific one. For example, spotting can be performed by spotting a solution of the oligonucleotide onto the substrate using a spotting machine. In this way, the oligonucleotide solution can be generally spotted substantially in a circle.

(6) Detection Instrument Using Protein of the Present Invention or its Partial Fragment A detection instrument of the present invention uses, as a probe, at least part of the amino acid sequence of the protein of the present invention. In other words, the detection instrument of the present invention is a detection instrument having the protein of the present invention or its partial fragment (fragment) immobilized thereto. The detection instrument can be used to detect and/or measure, under various conditions, a substance (e.g., a polypeptide, a nucleic acid, or an antibody) which interacts with the protein of the present invention.

The detection instrument of the present invention may be, for example, one including a substrate (support) having the probe immobilized thereto, which probe specifically binds to an antibody recognizing the protein of the present invention. For an amino acid sequence used as the probe, it is preferable to use a site of the protein of the present invention which site specifically interacts with the antibody of the present invention, i.e., an epitope-bearing peptide of the protein of the present invention.

A material of the substrate for use in the detection instrument of the present invention only needs to be one on which an oligopeptide can stably be immobilized. Examples of the material encompass, but are not limited to, synthetic resins (e.g., polycarbonate and plastic) and glass. A shape of the substrate is also not limited to any specific one. For example, a plate-shaped substrate or a film-shaped substrate may preferably be used.

Further, a method for immobilizing an oligopeptide on the substrate may be a conventionally-known method, and is not limited to any specific one. For example, immobilization may be performed by: a method in which an oligopeptide is bound to an insoluble carrier by means of a covalent bonding method or an adsorption method; an entrapping immobilization method in which an oligopeptide is surrounded by high-molecular substances; or a method in which an oligopeptide is immobilized on a support by using a cross-linking agent or the like. Note that a suitable immobilizing method may be selected considering (i) compatibility between a substrate for immobilization and an oligopeptide and (ii) a purpose of use of an immobilized substance.

(7) Usefulness of Gene, Protein, and Others of the Present Invention

As described above, the gene and the protein of the present invention are expressed specifically during latent infection with a herpesvirus. This protein is considered to have ability to induce a mental disorder in a host by being expressed in glial cells (e.g., astrocytes) in the brain.

Further, interestingly, the gene and the protein of the present invention have been found to be related to patients with mental disorders. Stated in greater detail, as shown in the later-described Example, an anti-SITH-1 antibody was detected in about 50% of patients suffering from mood disorders or other mental disorders, whereas the anti-SITH-1 antibody was hardly detectable in healthy persons (the frequency of detection of the anti-SITH-1 antibody in healthy persons was less than about 2%).

Thus, the present inventors have discovered on their own that an antibody specific to the protein of the present invention is found significantly only in patients with mood disorders and other mental disorders, but is hardly detectable in healthy persons. Note that the "mental disorder" as used herein is intended to mean such a state that the daily life or social life undergoes considerable limit on account of disorders in mental functions such as consciousness, intelligence, memory, emotions, thought, and behavior. The "mood disorder" is intended to mean such a state that because of persistent mood or emotional changes, abnormally depressive or related feelings are experienced to bring disturbances into daily life functioning or social life functioning.

Specific reasons for the above state where "an antibody specific to the protein of the present invention is found significantly only in patients with mood disorders and other mental disorders, but is hardly detectable in healthy persons" are now being under a diligent study to be unraveled. The protein of the present invention has such a nature that it is actively produced at the intermediate stage where latent infection is induced toward reactivation. It is believed that in response to a stress, reactivation of herpes viruses (e.g., HHV-6) is induced, whereby the protein of the present invention is produced. Persons who have the antibody against the protein of the present invention, accounting for about 50% of patients with mental disorders, are considered to have that protein expressed abundantly due to stress or any genetic factor for a prolonged period in glial cells (e.g., astrocytes) in the brain, which glial cells are latently infected with HHV-6. As a result, an increase of a calcium concentration in glial cells (e.g., astrocytes) continues for a prolonged period, and serotonin metabolism and other important functions of glial cells (e.g., astrocytes) are impaired, whereby a mental disorder would manifest itself. Chronic fatigue syndrome (CFS) patients who present with mental disorders carry the antibody against the protein of the present invention with a high frequency. The reason for this would be that the CFS patients are often latently infected with greater numbers of HHV-6 than healthy persons are, thus having a greater likelihood for the production of the protein of the present invention (protein SITH-1). The fact that the CFS patients are latently infected with greater numbers of HHV-6 than healthy persons are is also supported by the result of the reaction between the previously reported latent infection specific gene product and the antibody in CFS patients (see Non-Patent Document 5).

Thus, although a detailed mechanism of the phenomenon that the antibody against the protein of the present invention is found in patients with mental disorders has not been unraveled yet, utilizing this phenomenon provides a determination method and a diagnosis method contributing to objective diagnosis of mental disorders. Further, the present invention also relates to a determination kit, a diagnosis kit, an animal model producing method, and a drug screening method. The following describes each of these methods in detail.

(7-1) Determination Method of the Present Invention

The determination method of the present invention only needs to be a method for determining whether or not an antibody recognizing the protein of the present invention (i.e., the protein (a) or (b)) exists in a subject. Note that the term "subject" means a human or a mammal other than a human.

An assay for an antibody is enabled by detection through, for example, a reaction for binding to a protein recognized by the antibody or a partial fragment of the protein. Thus, in this determination method, a protein recognized by the antibody or a partial fragment of the protein is preferably used to determine for the presence of the antibody in an immunological manner (i.e., using an antigen-antibody reaction). Note that the "partial fragment" preferably contains at least an epitope-bearing peptide.

To give an example of this determination method, an insoluble carrier on which the protein according to the present invention or a partial fragment thereof is immobilized is brought into contact with a biological sample taken from a subject and washed, and then antibodies specifically bound to the protein or the partial fragment thereof on the insoluble carrier are detected. The antibodies specifically bound to the protein or the partial fragment thereof on the insoluble carrier are, for example, antibodies derived from the subject. Therefore, such the antibodies can be easily detected using a secondary antibody, i.e., an antibody specific to the antibodies in the subject. In this case, a dye, an enzyme or a radioactive or fluorescent label may be incorporated in the secondary antibody so as to enhance and thereby further facilitate the intended detection.

Thus, antibody assays to be used in the determination method under consideration include assay techniques that make use of traditional immunohistological approaches such as a fluorescent antibody technique, a dot blot assay, a western blotting technique, enzyme-linked immunosorbent assay techniques (including ELISA and a sandwich ELISA technique), a radioimmunoassay technique (RIA), and an immunodiffusion assay technique. These assays use molecules such as avidin and biotin for the purposes of molecular immobilization and detection, and techniques for preparing these reagents and methods of use thereof may be technologies known to a person skilled in the art. Note that the result of the determination method under consideration is an immunohistological stain of tissue sections for pathological testing.

Note also that the determination method under consideration is preferably performed using a biological sample isolated from the subject. The term "biological sample isolated" may cover any sample that contains cells, tissues or disrupted pieces thereof as taken from the subject. For example, the "biological sample isolated" may be any of peripheral blood, saliva, urine, stools, and cell samples, and is not limited to any specific one. Among these, particularly preferable sample is peripheral blood taken from the subject, in view of the fact that herpes viruses latently infect macrophages in peripheral blood. In this case, the subject benefits from a low degree of invasion.

An amount of antibodies present in a biological sample (sample) can be readily calculated by making comparison with an amount of antibodies present in a standard preparation (e.g., a standard sample taken from a healthy person or one taken from a typical patient with a mental disorder), using e.g., a linear regression computer algorithm. While various assay techniques are available for antibody detection, an example for ELISA is described in Iacobelli et al., Breast Cancer Research and Treatment 11: 19-30 (1988).

Suitable enzyme labels may be exemplified by those derived from a class of oxidases which catalyze the generation of hydrogen peroxide through reaction with the substrate. Glucose oxidase is particularly preferable, since it has satisfactory stability and its substrate (glucose) is easily available. Activity of the oxidase label can be assayed by measuring a concentration of hydrogen peroxide formed by an enzyme-labeled antibody/substrate reaction. In addition to enzymes, other suitable labels include radioisotopes (e.g., iodine ($^{125}$I and $^{121}$I), carbon ($^{14}$C), sulfur ($^{35}$S), tritium ($^{3}$H), indium ($^{112}$In), and technetium ($^{99m}$Tc), as well as fluorescent labels (e.g., fluorescein and rhodamin) and biotin.

A level of antibodies (against the protein of the present invention) that are present in biological samples obtained from the subject can also be detected in vivo by methods other than the above-described immunoassay technique, for example, by image analysis. In short, in view of the fact that the antibody against the protein according to the present invention is also a protein, an antibody that specifically recognizes this antibody may be used for in vivo detection by image analysis of the level of the antibodies (against the protein of the present invention) that are present in the biological samples obtained from the subject.

Antibody labels or markers for the in vivo image analysis of antibodies encompass those that can be detected by X-ray imaging, NMR, or ESR. For X-ray imaging, suitable labels encompass radioisotopes such as barium or cesium that emit detectable radiation but that are clearly harmless to the sample under test. Suitable markers for NMR and ESR encompass those which can be used to label a nutrient for culturing an associated hybridoma to produce a corresponding antibody, whereby the label is incorporated in the antibody produced; an example of such label is deuterium having a detectable characteristic spin.

An antibody or a fragment thereof that is specific for the antibody against the protein of the present invention and that is labeled with a suitable, detectable image-analysis portion, such as a radioisotope (e.g. $^{111}$In or $^{99m}$Tc), a radio-opaque substrate or a substance detectable by nuclear magnetic resonance is introduced (e.g., parenterally, subcutaneously, or intravenously) into a mammal to be tested for a disorder. It will be understood in the art of interest that a quantity of the image-analysis portion required for generating a diagnostic image is determined by the size of the sample under test and the image analysis system to be used. In the case where that portion is part of a radioisotope, a quantity of radioactivity to be injected into a human sample is typically in a range from about 5 to about 20 mCi of $^{99m}$Tc. Subsequently, the label antibody or the fragment thereof is accumulated preferentially at a site of the cell which site including the antibody against the protein of the present invention. Note that an in vivo image analysis of tumors is described in S. W. Burchiel et al., "Immunopharmacokinetics of Radiolabeled Antibodies and Their Fragments" (Turner Imaging, Chapter 13: The Radiochemical Detection of Cancer, Burchiel, S. W. and Rhodes, B. A. eds., Masson Publishing Inc. (1982)).

The following lists specific examples of a label available for the present invention. Examples of suitable enzyme labels include malate dehydrogenase, Staphylococcus nuclease, yeast alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotope labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, and $^{109}$Pd. Indium 111 ($^{111}$In) is a preferred isotope in the case where in vivo imaging is employed, since this avoids a problem of dehalogenation of a monoclonal antibody labeled with $^{125}$I or $^{131}$I, which dehalogenation is caused by a liver. Further, this radionuclide has a favorable gamma release energy for imaging (Perkins et al., Eur. J. Nucl. Med. 10: 296-301 (1985); Carasquillo et al., J. Nucl. Med. 28: 281-287 (1987)). For example, indium 111 ($^{111}$In) coupled to a monoclonal antibody using 1-(P-benzyl isothiocyanate)-DPTA has shown little uptake in non-tumorous tissues, particularly a liver, and therefore enhances specificity of tumor localization (Esteban et al., J. Nucl. Med. 28: 861-870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include $^{152}$Eu label, fluorescein label, isothiocyanate label, rhodamin label, phycoerythrin label, phycocyanin label, allophycocyanin label, o-phthalaldehyde label, and fluorescamine label.

Examples of suitable marker toxins include diphtheria toxin, ricin, and cholera toxin.

Examples of chemiluminescent labels include luminal label, isoluminal label, aromatic acridinium ester label, imidazole label, acridinium salt label, oxalate ester label, luciferin label, luciferase label, and aequorin label.

Examples of contrast agents for nuclear magnetic resonance include heavy metal atomic nuclei such as Gd, Mn, and Fe.

Representative techniques for binding the above-mentioned labels to antibodies are provided by Kennedy et al. (Clin. Chim. Acta 70:1-31 (1976)) and Schurs et al. (Clin. Chim. Acta 81: 1-40 (1977)). Coupling techniques described in the latter include a glutaraldehyde method, a periodate method, a dimaleimide method, and a m-maleimidebenzyl-N-hydroxy-succinimide ester method. All of these methods are incorporated herein by reference.

(7-2) Diagnosis Method

The diagnosis method of the present invention only needs to use the above determination method. Specific configuration, conditions and others of the diagnosis method are not particularly limited. For example, by using as a marker the antibody of the present invention existing in a human subject or an animal subject, it is possible to determine that the human subject or the animal subject contacts a mental disorder. Further, diagnosis may be performed by using as an indication a quantitative value of the antibody of the present invention as follows: A threshold value is appropriately set according to a quantitative value (normal value) measured in a healthy person or a quantitative value (disorder value) measured in a typical patient with mental disorders; if a value measured in a subject is above or below the threshold value, the subject is determined to contract a mental disorder with a high probability. Once a mental disorder is developed, an amount of the antibody is increased. In view of this, in the present invention, for example, a quantitative value (normal value) measured in a healthy person is set as a threshold value; if a value measured in a human subject is below the threshold value, the human subject can be determined to contract a mental disorder with a high possibility.

Note that the term "human subject" herein means a human, and the term "animal subject" means an animal other than a human. Examples of the animal subject encompass mice, rats, and monkeys. Not only that, any animal other than a human can be the "animal subject".

Thus, this diagnosis method makes it possible to easily and accurately determine (i) whether or not a subject has a mental disorder or (ii) whether or not a subject has a possibility of contracting a mental disorder. Further, the diagnosis method for an animal subject will be quite useful for e.g., drug screening for development of therapeutic agents for mental disorders and animal subjects for testing drug effectiveness.

(7-3) Determination Kit, Diagnosis Kit

Each of a determination kit and a diagnosis kit of the present invention only needs to be designed to allow the determination method described in the above (7-1) or the diagnosis method described in the above (7-2) to be performed. Specific configurations, materials, instruments and others of these are not specifically limited. To be specific, in order to immunologically detect the antibody of the present invention, each of the determination kid and the diagnosis kit preferably includes any of: (i) a protein of the present invention; (ii) a partial fragment (preferably including an epitope-bearing peptide) of the protein (i); and (iii) a detection instrument to which the protein (i) or the partial fragment (ii) is immobilized.

A kit having the above configuration is quite useful, since such a kit makes it possible to easily and reliably perform the determination method or the diagnosis method of the present invention.

Further, in addition to the above configuration, each of the determination kit and the diagnosis kit may include an item for performing each step of the determination method or the diagnosis method. Examples of such an item encompass: instruments for taking a sample from a subject (e.g., a syringe (injector) for collecting peripheral blood); and items required for performing the determination method and/or the diagnosis method such as laboratory instruments and various reagents (e.g., reagents used for an immunological reaction such as ELISA). Further, each of the determination kit and the diagnosis kit may include an arithmetic unit (e.g., a computer) or software each of which is required for performing the determination more easily and accurately.

(7-4) Methods for Producing, Determining, Screening, and Evaluating Animal Model The diagnosis method of the present invention is applicable to: a method for producing an animal model (other than a human) of a mental disorder; a method for determining usefulness of the animal model; and a method for determining usefulness of a drug by means of drug screening using the animal model. Specifically, as described in the Example, the animal model of the mental disorder can be produced by introducing the protein SITH-1 into the brain of an animal using e.g., a vector. Further, usefulness of the animal model of the mental disorder can be determined as follows: Similarly to the determination method and the diagnosis method, it is determined whether or not an animal subject develops a mental disorder, depending on the presence or absence of the antibody of the present invention; if the animal subject has developed the mental disorder, the animal subject can be determined to be useful as the animal model of the mental disorder.

It is more preferable that each of the above various methods additionally uses, as evaluation means, a diagnosis method utilizing e.g., a heretofore known behavior disorder and/or startle response of an animal. Specifically, for diagnosis in animal tests, any of the followings may be employed: (i) a test for a behavior disorder, e.g., a tail suspension test or a forced swimming test; and (ii) a known brain function test, e.g., startle response.

The "subject animal" herein may be any animal other than a human, particularly preferable examples of which encompass mice, rats, guinea pigs, dogs, rabbits, monkeys, and jockos. Determination (diagnosis) of mental disorders for animals other than a human was more difficult. In terms of this, the method of the present invention is quite useful.

Further, a candidate substance for a psychotropic agent or an antipsychotic agent (an agent for treating or improving a mental disorder) may be administered to such an animal model, and thereafter a test for the behavior disorder and detection of the antibody of the present invention may be performed in a manner as described above. Then, if the mental disorder is cured or improved, the candidate substance can be determined to have an anti-mental disorder effect. Thus, use of the diagnosis method of the present invention makes it possible to easily and reliably perform screening for a candidate substance for a psychotropic agent. The "candidate substance for a psychotropic agent" herein may be any substance desired by a person who conducts the test.

Note that the point of the determination method, the diagnosis method or the like of the present invention is to provide an objective determination method for determining whether or not a subject contracts a metal disorder by detection of an antibody against a protein which is expressed specifically during latent infection with a herpesvirus, and does not lie in each manipulation specifically described herein. Therefore, it should be noted that determination methods and diagnosis methods using manipulations other than those described above are also encompassed in the scope of the present invention.

In addition, infection with herpesviruses is considered to be related to: diseases accompanied by immunodeficiency such as CFS, which is described also in the Example, (e.g., autoimmune diseases such as Crohn's disease); cutaneous diseases which are considered to be associated with HHV-6 (e.g., drug-induced hypersensitivity syndrome); and encephalitis and encephalopathy induced by HHV-6. Therefore, it would be considered that the determination method and the diagnosis method of the present invention also enable objective diagnosis and evaluation of these diseases.

That is, the protein, the gene and others of the present invention can be used as a disease marker for various diseases which might be involved with HHV-6.

Further, the present invention also encompasses an animal model produced by transfer of the above-described gene of the present invention, a gene product thereof (e.g., a protein encoded by the gene), or a recombinant expression vector having the gene. Since the gene of the present invention is involved in a mental disorder as described above, the animal model produced by transfer of the gene, the gene product thereof (e.g., the protein encoded by the gene), or the recombinant expression vector having the gene manifests a symptom of the mental disorder. Examples of the symptom of the mental disorder encompass manic-depressive-like symptoms, mania-like symptoms, depression-like symptoms, and, depending on the test method, schizophrenia-like symptoms.

A subject animal is not limited to any specific one, as long as it is available as a test animal. Particularly preferable one is a mammal, for example, a mouse, a rat, or a monkey.

Furthermore, a method for transfer of the gene, the gene product, and the recombinant expression vector may be a conventionally-known method, and is not limited to any specific one. For example, a method for causing the protein of the present invention to be expressed in a brain can be a method using an adenovirus vector or a method using a retrovirus vector (see the later-described Example), and, of course, can be any of methods using vectors which are not the adenovirus vector or the retrovirus vector. Alternatively, gene transfer using a general transgene (e.g., production of a transgenic mouse) can be used. Further alternatively, a method for directly inoculating the protein of the present invention into a brain can be used.

The animal model of the mental disorder can be suitably used for e.g., study on treating methods for mental disorders, study on effects of drugs, determination of effects of drugs, and evaluation of treating methods (e.g., thermotherapy) which are not treating methods using drugs, and therefore is quite useful.

Further, the animal model can be used for study on a factor related to a development factor of a mental disorder. The animal model can also be used for research of prevention of development of mental disorders e.g., by studying how much fatigue and stress are involved in induction of a mental disorder.

The following shows Examples to describe the embodiments of the present invention in greater detail. Needless to say, the present invention is not limited to the Examples below, and various forms may be taken for the details. Further, the present invention is not limited to the description of the embodiments above, but may be altered by a skilled person within the scope of the claims. An embodiment based on a proper combination of technical means disclosed in different embodiments is encompassed in the technical scope of the present invention.

Examples

<1. Identification of Gene Product (mRNA) Encoding Latent Infection Specific Protein SITH-1>

Messenger RNA (mRNA) was separated from those macrophages described in Non-Patent Document 1 that were latently infected with HHV-6, and a reverse transcription reaction was performed using random primers, IE4RB as a primer for reverse transcription of sense transcripts, and IE2FB as a primer for reverse transcription of anti-sense transcripts. Thereafter, the resultant reverse transcripts (cDNA) were amplified by the PCR technique using the primers IE4RB and IE2FB, and the products were further amplified by the double-nested PCR technique using the inner primers IE4RA and IE2FA. FIG. 1 shows (i) the correspondence between the sense transcript (H6LT) of the known mRNA during productive infection and the novel latent infection specific gene and (ii) an open reading frame of the latent infection specific protein SITH-1. For details of the sequence information about SITH-1 and the novel latent infection specific gene, see the SEQUENCE LISTING.

As a result, the amplification yielded a 925-bp product, which differed both from (i) a 351-bp product amplified from mRNA being expressed in MT-4 cells that were productively infected with HHV-6 and (ii) a 351-bp product amplified from a latent infection specific gene product (HHV-6 latency-associated transcript: H6LT), described in Non-Patent Document 3, that was detectable during latent infection of macrophages (MΦ) with HHV-6.

This product was also different from a 1241-bp product amplified from HHV-6 DNA in that it was solely amplified from the product of the reverse transcription of the anti-sense transcripts in the cells latently infected with HHV-6. From this, this product was shown to be a heretofore unknown, novel latent infection specific gene product (see FIG. 2). In FIG. 2, "R" signifies a random primer, "S" signifies a sense transcript, and "anti-S" signifies an anti-sense transcript.

Figure 3:
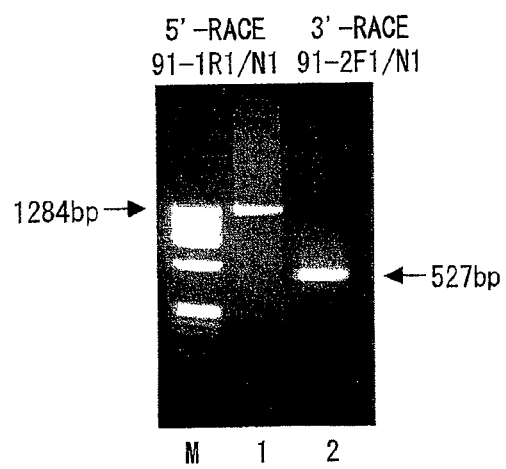
FIG. 3 is a diagram showing the results of analysis performed by the RACE technique with respect to novel latent infection specific gene mRNAs.

To determine the structure of this novel latent infection specific gene mRNA, a 5'-rapid amplification of cDNA ends (RACE) method and a 3'-RACE method were performed, whereby not only the 5'- and 3'-ends but also the overall nucleotide sequence was determined (see FIG. 3).

```
                                         (SEQ ID NO: 4)
    IE4RB:  5'-GATGCTCCTTCTTCCACATTACTGG-3'

(SEQ ID NO: 5)
    IE2FB:  5'-CATCCCATCAATTATTGGATTGCTGG-3'

(SEQ ID NO: 6)
    IE2FA:  5'-GAAACCAC-CACCTGGAATCAATCTCC-3'

(SEQ ID NO: 7)
    IE4RA:  5'-GACACATTCTTGGAAGCGATGTCG-3'

(SEQ ID NO: 8)
    N1:     5'-GCTGGGTAGTCCCCACCTTTCTAGA-3'

(SEQ ID NO: 9)
    αF1:    5'-CTGAAGCATGTAAGCACATCTCTTGC 3'

(SEQ ID NO: 10)
    αR1:    5'-GCTTCGAGATCAGTAGTGGTACG-3'
```

<2. Functional Analysis of Novel Latent Infection Specific Gene Protein SITH-1>

Figure 4:
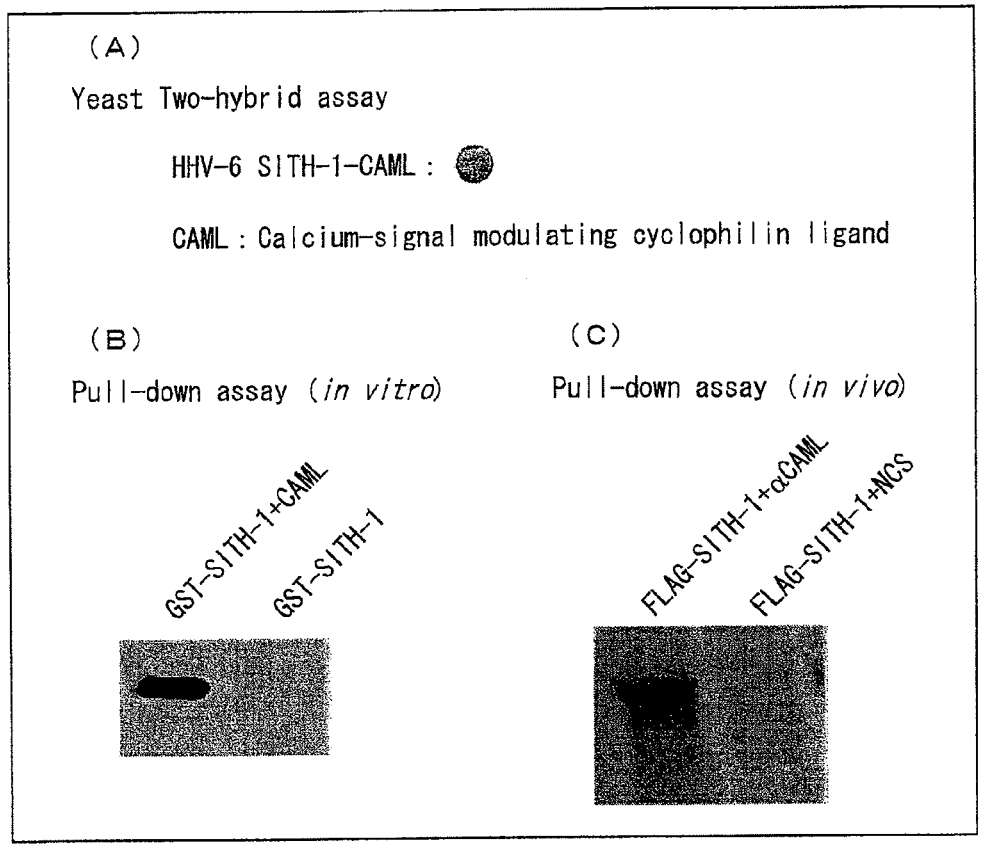
FIG. 4 is a diagram showing the results of an experiment in which a host protein binding to the protein SITH-1 was identified by the yeast two-hybrid assay.

To study the function of the protein SITH-1, a host protein to which the protein SITH-1 would bind within cells was identified. This was performed by screening of a human fetal brain cDNA library by means of yeast two-hybrid assay with the protein SITH-1 used as a bait. The result is shown in FIG. 4. In FIG. 4, (A) shows yeast clones in which β-galactosidase was strongly expressed owing to binding between SITH-1 and CAML; (B) shows a diagram verifying by western blotting and staining of anti-CAML antibodies that, in the in vitro pull-down assay, CAML expressed in *E. coli* could be co-precipitated with a GST-SITH-1 fusion protein which was also expressed in *E. coli*; and (C) shows a diagram verifying by western blotting and staining of anti-FLAG antibodies that, after SITH-1 with a FLAG tag and CAML were transferred into 293T cells using an expression vector, the SITH-1 could be co-precipitated with anti-CAML antibodies. As FIG. 4 shows, the protein SITH-1 was found to bind strongly to the calcium-signal modulating cyclophilin ligand (CAML).

Figure 5:
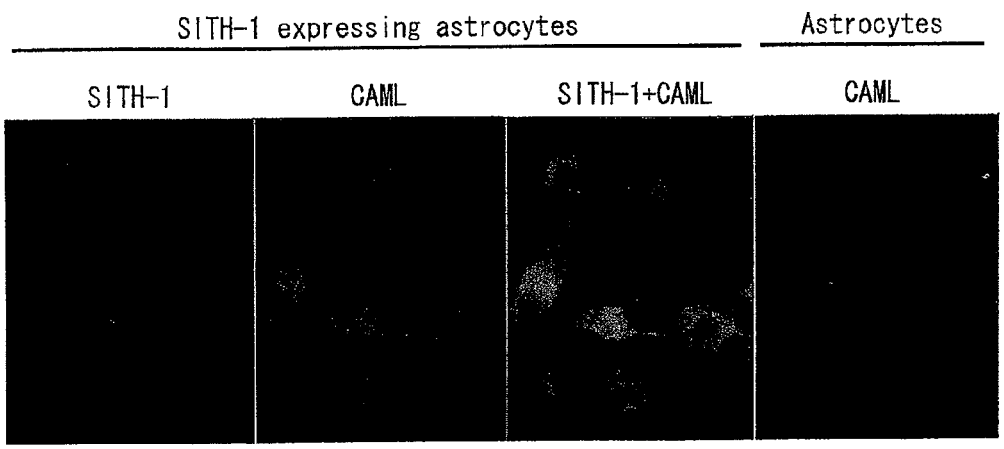
FIG. 5 is a diagram showing that a protein SITH-1 increased an amount of CAML in an astrocyte-like glial cell line.

CAML is a protein that has been reported to show strong expression in lymphocytes and in a brain, and it is known that CAML has ability to increase an intracellular calcium concentration. Thus, in order to see whether the protein SITH-1 would be mediated by CAML to increase the intracellular calcium concentration, both an astrocyte-like glial cell line (U373) in which SITH-1 had been expressed and untreated U373 cells were stained by the fluorescent antibody technique using anti-SITH-1 antibodies and anti-CAML antibodies. As it turned out, when the protein SITH-1 was expressed in the astrocyte-like glial cell line (U373), more CAML was found than in the untreated U373 cells (FIG. 5). A level of CAML expression in U373 cells was not very high when the U373 cells were untreated, but more CAML was found to occur by expressing SITH-1 in the U373 cells.

Figure 6:
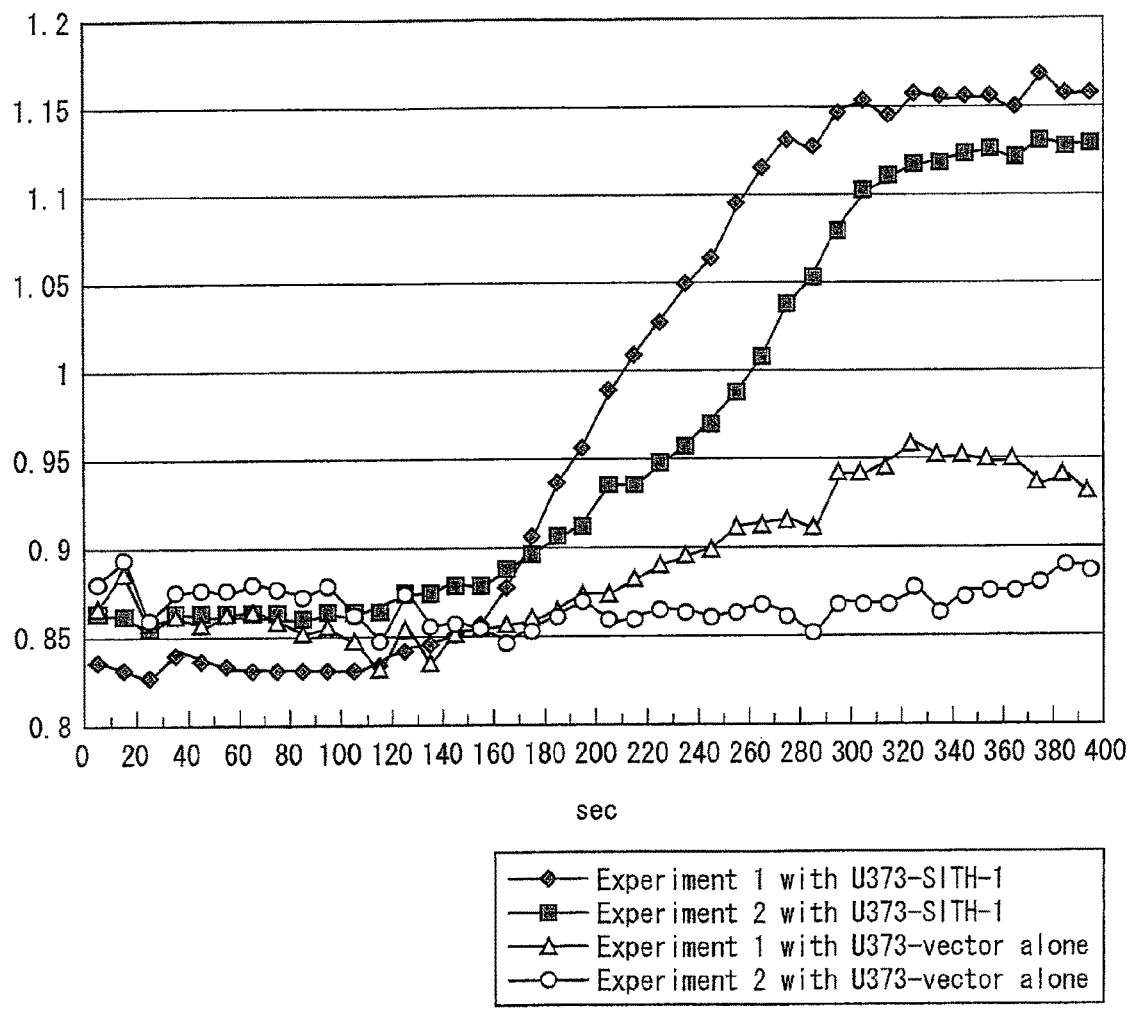
FIG. 6 is a diagram showing how SITH-1 increased a calcium concentration in glial cells.

In another experiment, two samples were prepared; one sample was prepared by transferring SITH-1 into an astrocyte-like glial cell line (U373) via a retrovirus vector, and the other sample was prepared by introducing only the vector into U373. Each sample was stimulated with thapsigargin (TG), and an intracellular calcium concentration was measured using Fura2. As a result, the actual measurement of the intracellular calcium concentration showed that on account of the stimulation with thapsigargin (TG), the intracellular calcium concentration in the SITH-1 expressing astrocyte-like glial cell line was considerably higher than in the cells into which only the vector had been transferred (FIG. 6).

From those results, it was found that the protein SITH-1 has ability to increase an intracellular calcium concentration in an astrocyte-like glial cell line by being expressed during latent infection with HHV-6 to increase an amount of intracellular CAML.

<3. Relationship Between SITH-1 and Mood Disorders>

Figure 7:
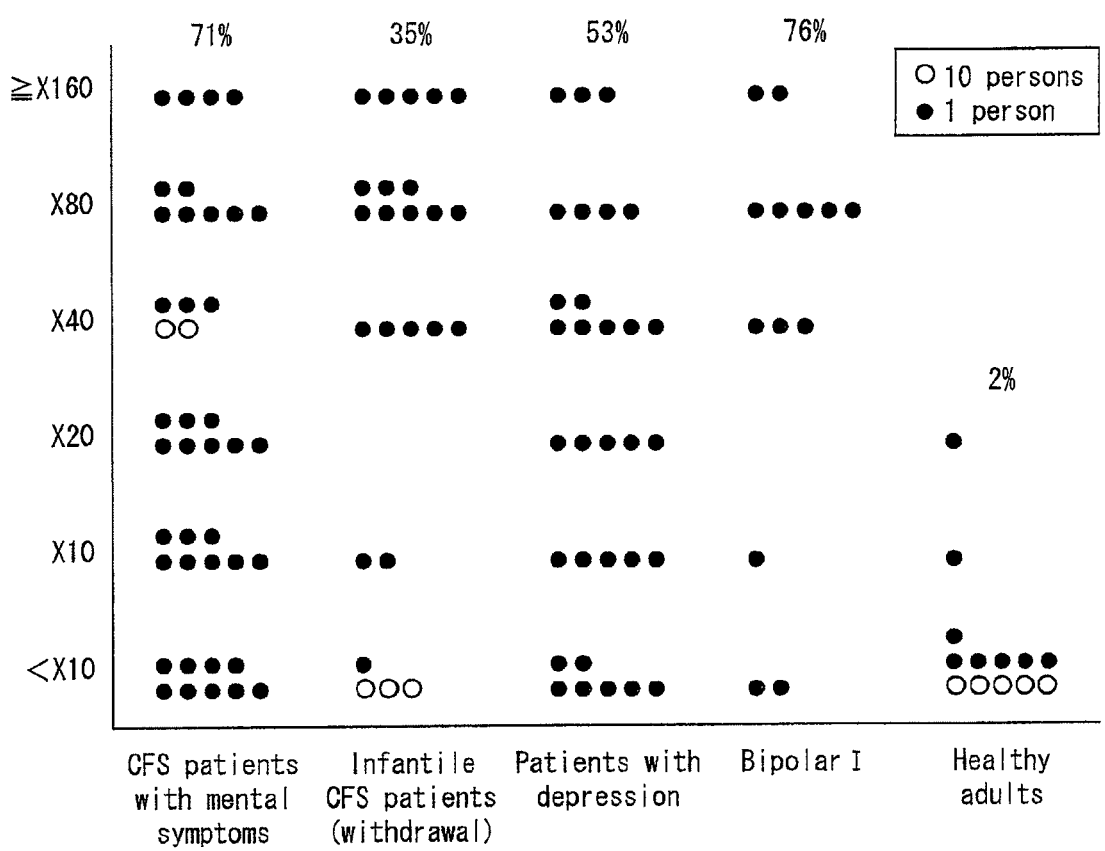
FIG. 7 is a graph showing antibody titers to SITH-1 in patients with mental disorders.

In the next step, the present inventors studied the relationship between SITH-1 and mental disorders. The results are shown in FIG. 7. Unlike the latent infection specific gene protein reported in e.g., Non-Patent Document 5, the relationship between an antibody against SITH-1 and patients with chronic fatigue syndrome was low, but the frequency of antibody carriers was high among patients with chronic fatigue syndrome accompanied by mental disorders. In many cases, the patients with chronic fatigue syndrome (CFS) accompanied by psychiatric symptoms primarily manifested depressive symptoms, whereas infantile CFS patients mainly presented with abnormal agitation. In FIG. 7, "bipolar I" refers to patients with manic-depressive illness of severe symptoms. Healthy adults scarcely carried the antibody against SITH-1. For antibody titer measurement, SITH-1-expressing 293T cells were used as antigens, and the fluorescent antibody technique was applied.

<4. Construction of Model Mice of Mental Disorder by Expressing SITH-1>

SITH-1 having a glial fibrillary acidic protein (GFAP) promoter linked upstream of its open reading frame was injected into the brains of newborn mice using an adenovirus vector or a retrovirus vector. GFAP is a protein expressed specifically in glial cells such as astrocytes. About four or five weeks after the injection, behavior of each mouse was observed to confirm that model mice with mental disorders were established by transfer of SITH-1.

Figure 8:
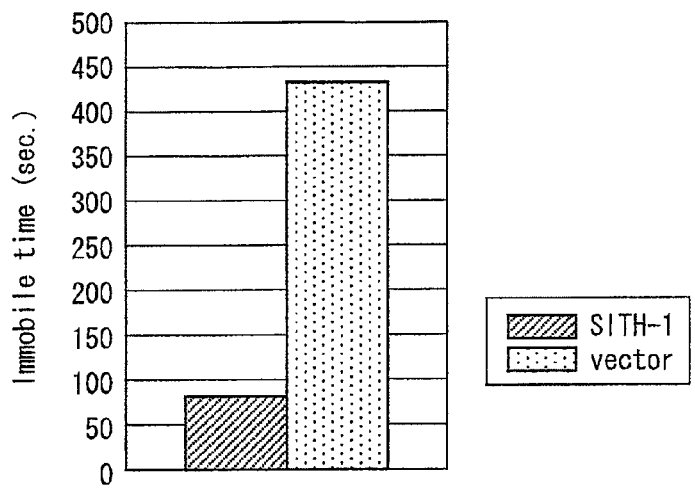
FIG. 8 is a graph showing the result of investigating an effect of SITH-1 in a tail suspension test.
Figure 9:
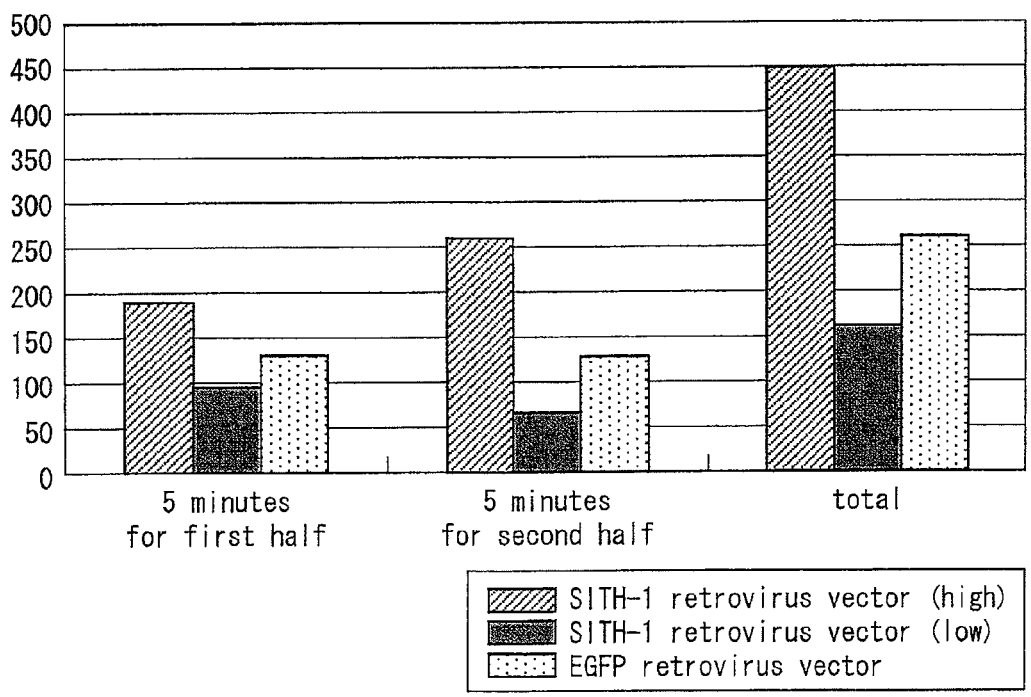
FIG. 9 is a graph showing the result of investigating an effect of in a forced swimming test.

A tail suspension test and a forced swimming test were conducted to evaluate mental disorders; these tests are commonly used to observe patients with depression or manic-depressive illness. Specifically, mice into which SITH-1 was transferred using an adenovirus vector were subjected to a tail suspension test. As it turned out, the mice into which SITH-1 was transferred had a markedly shorter immobile time, indicating that these mice were in a manic state (FIG. 8). Subsequently, mice into which SITH-1 was transferred using a retrovirus vector were subjected to a forced swimming test. As it turned out, the mice into which SITH-1 was transferred using the retrovirus vector at HIGH titer had a longer immobile time than control mice into which an enhanced green fluorescent protein (EGFP) gene was transferred, indicating that the mice into which SITH-1 was transferred at HIGH titer were in a state of depression. In contrast, mice into which SITH-1 was transferred using the retrovirus vector at LOW titer had a shorter immobile time, indicating that the mice into which SITH-1 was transferred at LOW titer were in a manic state (FIG. 9). Thus, the manic state was observed in the tail suspension test, whereas both the manic state and the depressed state were observed in the forced swimming test. In addition, the fact that either the manic state or the depressed state was observed depending on the titer of the retrovirus vector used to introduce SITH-1 not only shows that the model of interest can serve as models of depression and manic-depressive illness alike, but also suggests that an amount of expression of SITH-1 affects symptoms of mental disorders.

Figure 10:
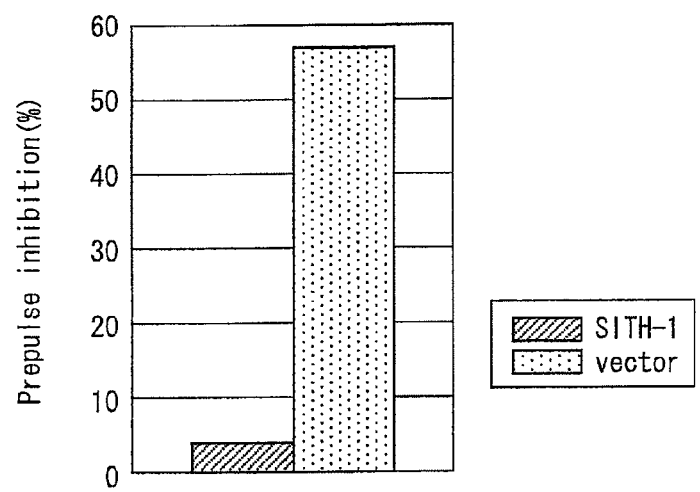
FIG. 10 is a graph showing the result of investigating an effect of SITH-1 in terms of startle response (prepulse inhibition).

The present inventors also measured a prepulse inhibition in order to check for any abnormality in a startle response, which abnormality is to be found in patients with manic-depressive illness and schizophrenia. Specifically, mice into which SITH-1 was transferred using the adenovirus vector were evaluated for a startle response by measuring the prepulse inhibition. The result is shown in FIG. 10; as it turned out, the SITH-1 transferred mice had a markedly lower prepulse inhibition, indicating that these mice had become overly sensitive to stimuli. Thus, considerable abnormality was also observed in the startle response, indicating that SITH-1 greatly affects a brain function associated with mental disorders.

<5. Construction 2 of Model Mice of Mental Disorder by Expressing SITH-1>

Next, an open reading frame of SITH-1 was linked downstream of a GFAP promoter, and expressed in glial cells of mice using an adenovirus vector; three weeks later, the mice were measured for their motor activity in terms of wheel running activity. The result is shown in FIG. 11.

Figure 11:
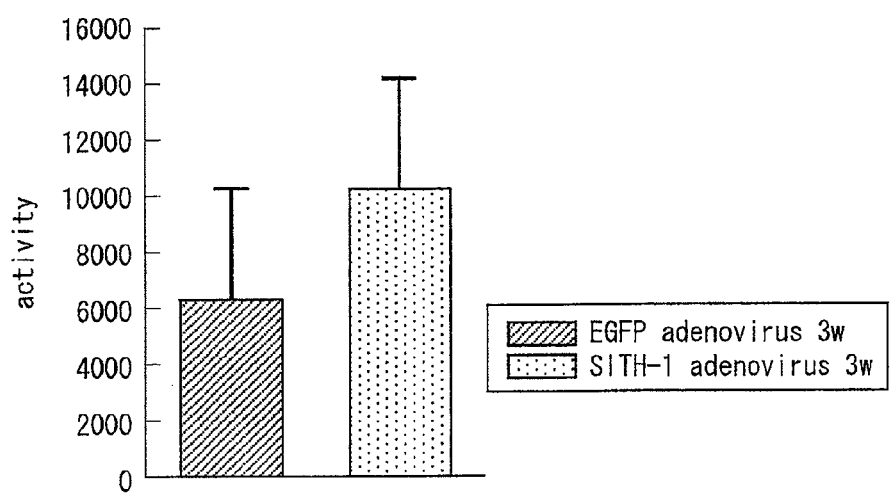
FIG. 11 is a graph showing the result of an experiment in which SITH-1 was expressed in mouse glial cells using an adenovirus vector and, three weeks later, the animals were measured for their motor activity under wheel running activity.

As FIG. 11 shows, compared to control mice in which EGFP (enhanced green fluorescent protein) was expressed, the SITH-1 expressing mice had their motor activity enhanced, and the SITH-1 expressing mice showed a tendency to be in a manic state.

<6. Construction 3 of Model Mice of Mental Disorder by Expressing SITH-1>

Subsequently, an open reading frame of SITH-1 was linked downstream of a GFAP promoter, and expressed in glial cells of mice using a lentivirus vector; eight weeks later, the mice were measured for their motor activity in terms wheel running activity. The result is shown in FIG. 12.

Figure 12:
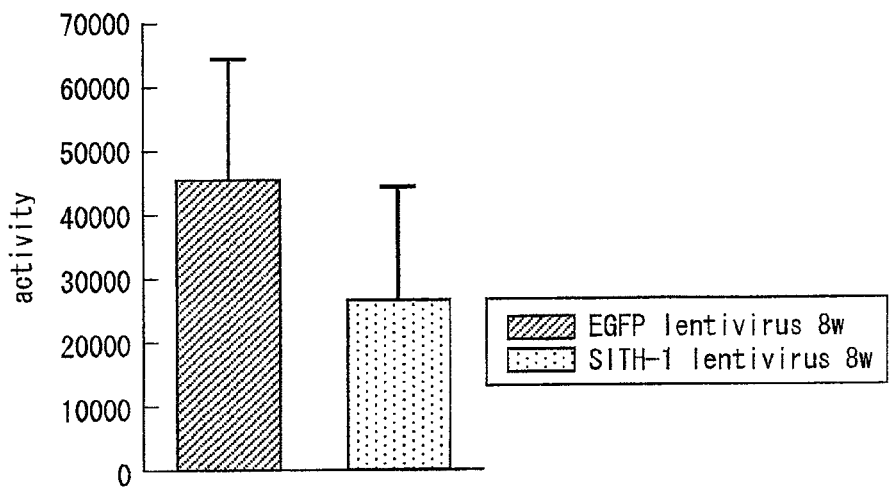
FIG. 12 is a graph showing the result of an experiment in which SITH-1 was expressed in mouse glial cells using a lentivirus vector and, eight weeks later, the animals were measured for motor activity under wheel running activity.

As FIG. 12 shows, compared to control mice in which EGFP (enhanced green fluorescent protein) was expressed, the SITH-1 expressing mice had their motor activity suppressed, and the SITH-1 expressing mice showed a tendency to be in a depressed state.

As can be seen from FIGS. 11 and 12, the same SITH-1 was found to cause two opposite phenomena, a manic state and a depressed state. The reasons would be as follows: 1) SITH-1 carried by the adenovirus vector was expressed in a greater amount than when SITH-1 was carried by the lentivirus vector; 2) on the other hand, the lentivirus vector allowed SITH-1 to be expressed for a longer period, so the effect of the prolonged expression of SITH-1 was observed.

This fact, i.e., model mice of a manic state and a depressed state can both be constructed by expressing SITH-1, may be described as providing a result in good agreement with a clinical finding that antibodies against SITH-1 are detected both from patients with manic-depressive illness and from patients with depression.

<7. Diagnosis Using SITH-1 as Marker>

A study was made to see if diagnosis based on SITH-1 would also be useful in diagnosing other diseases complicated by depression. The results are shown in FIG. 13.

Diagnosis based on the anti-SITH-1 antibody is quite specific to mood disorders such as depression, manic-depressive illness, and chronic fatigue syndrome. However, as FIG. 13 shows, the same diagnosis exceptionally showed a high positive rate among patients with Crohn's disease. No positive outcome was shown by patients with ulcerative colitis which was similar to Crohn's disease.

Figure 13:
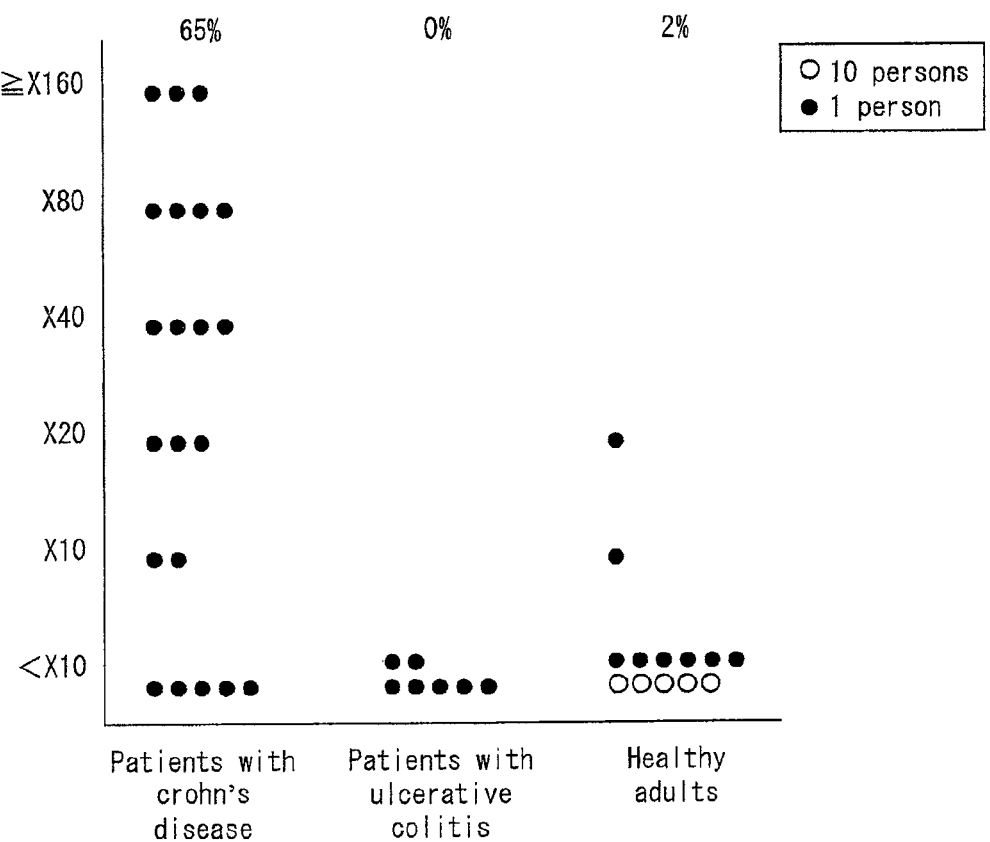
FIG. 13 is a graph showing the results of diagnosing, with SITH-1 used as a marker, various diseases that are complicated by depression.

However, it is known that Crohn's disease is most frequently complicated by "depressive symptoms", and the anti-SITH-1 antibody positive persons shown in FIG. 13 are cases of Crohn's disease that were serious enough to be complicated by depressive symptoms. The example under consideration shows that even in such serious cases that patients with Crohn's disease which is a chronic disease classified as an autoimmune disease also present with depressive symptoms, depression can be diagnosed using SITH-1 as a marker. In other words, testing with the anti-SITH-1 antibody may be considered to be "also useful in diagnosis of depression that is caused by other, non-psychiatric diseases."

INDUSTRIAL APPLICABILITY

As described above, each of a gene and a protein of the present invention is a factor involved in latent infection with a herpesvirus. By using the gene and/or the protein as a marker, it is possible to objectively determine whether or not a subject contracts a mental disorder. Therefore, the present invention not only provides benefits in academic fields and basic research fields, but also has significance in clinical medicine fields. Therefore, the present invention is applicable in various aspects of industry.

The invention claimed is:

1. A nucleic acid being one of the following nucleic acids (a) and (b):
   (a) a nucleic acid encoding a protein having the amino acid sequence shown in SEQ ID NO: 1, wherein said nucleic acid further comprises a fluorescent label or a chemiluminescent label attached to the nucleic acid; and
   (b) a nucleic acid comprising an open reading frame region having the nucleotide sequence shown in SEQ ID NO: 2, wherein said nucleic acid further comprises a fluorescent label or a chemiluminescent label attached to the nucleic acid.

2. A recombinant vector comprising:
   a vector; and
   a nucleic acid inserted into said vector being one of the following nucleic acids (a) and (b):
   (a) a nucleic acid encoding a protein having the amino acid sequence shown in SEQ ID NO: 1; and
   (b) a nucleic acid comprising an open reading frame region having the nucleotide sequence shown in SEQ ID NO: 2,
   wherein the recombinant vector comprises a promoter,
   wherein said promoter is selected from the group consisting of a CMV immediate-early promoter, a HSV thymidine kinase promoter, a phage λPL promoter, an E. coli lad promoter, an E. coli lacZ promoter, a T3 promoter, a T7 promoter, a gpt promoter, a λPR promoter, a trp promoter, a tac promoter, a GFAP promoter, a SV40 early promoter and late promoter, a retrovirus LTR promoter and a metallothionein promoter.

3. The recombinant vector according to claim 2,
   wherein the recombinant vector is any one of phage vectors, plasmid vectors, virus vectors, retrovirus vectors, chromosome vectors, episome vectors, vectors derived from bacterial plasmids, bacteriophages, yeast episomes, yeast chromosome elements and combinations thereof, and
   said virus is any one of baculoviruses, papovaviruses, vaccinia viruses, adenoviruses, avipoxviruses, pseudorabies viruses, lentiviruses, retroviruses and herpesvirus.

4. The recombinant vector according to claim 3, wherein the combinations thereof are cosmids and phagemids.

5. A host cell comprising the vector of claim 2, wherein the host is at least one selected from the group consisting of a bacterial cell, a fungus cell, an insect cell, an animal cell, a plant cell, *Caenorhabditis elegans* and oocyte cells of *Xenopus laevis*.

6. A recombinant vector comprising:
   a vector; and
   a nucleic acid inserted into said vector being one of the following nucleic acids (a) and (b):
   (a) a nucleic acid encoding a protein having the amino acid sequence shown in SEQ ID NO: 1; and
   (b) a nucleic acid comprising an open reading frame region having the nucleotide sequence shown in SEQ ID NO: 2,
   wherein the recombinant vector comprises an enhancer selected from the group consisting of a SV40 enhancer, an early promoter enhancer of a cytomegalovirus, a polyoma enhancer on the late side of a replication origin, and an adenovirus enhancer.

7. A host cell comprising the vector of claim 6, wherein the host is at least one selected from the group consisting of a fungus cell, an insect cell, an animal cell, a plant cell, *Caenorhabditis elegans* and oocyte cells of *Xenopus laevis*.

8. A nucleic acid being one of the following cDNA sequences (a) and (b):
   (a) a cDNA sequence encoding a protein having the amino acid sequence shown in SEQ ID NO: 1; and
   (b) a cDNA sequence comprising an open reading frame region having the nucleotide sequence shown in SEQ ID NO: 2.

9. A nucleic acid being one of the following DNA sequences (a) and (b):
   (a) a DNA sequence including no noncoding sequences encoding a protein having the amino acid sequence shown in SEQ ID NO: 1; and
   (b) a DNA sequence including no noncoding sequences comprising an open reading frame region having the nucleotide sequence shown in SEQ ID NO: 2.

* * * * *

SEQUENCE LISTING

<160> NUMBER OF SEQ ID NOS: 10

<210> SEQ ID NO 1
<211> LENGTH: 159
<212> TYPE: PRT
<213> ORGANISM: Human herpesvirus 6

<400> SEQUENCE: 1

```
Met Gly Tyr Glu Glu Lys Val Ser Ala Thr Gly Lys Thr Arg Leu Lys
1               5                   10                  15

Ile Leu Ala Cys Leu Ile Val Leu Ile Leu Ala Ala Ala Ile Thr Met
            20                  25                  30

Leu Thr Leu Glu Ile Ile Ser Asn Gln Lys Arg Thr Thr Thr Asp Leu
        35                  40                  45

Glu Ala Val Thr Val Ala Leu Lys His Val Ser Thr Ser Leu Ala Ser
    50                  55                  60

Cys Thr Glu Ser Thr Thr Ser Val His Thr Asp Ser Val Thr Ser Gln
65                  70                  75                  80

Pro Thr Lys Asn Lys Glu Ser Arg Lys Lys Ile Glu Gly Lys Ser Pro
                85                  90                  95

Ser Trp Val Gln Ala Leu Thr Thr Ala Ser Gly Ile Ile Leu Leu Phe
            100                 105                 110

Cys Ile Met Met Ile Phe Ile Thr Cys Ser Trp Thr Thr Glu Lys Asp
        115                 120                 125

Thr Glu Lys Ser Glu Val Gln Ser Tyr Ala Ser Ser Val Glu Thr Leu
    130                 135                 140

Asp Ser Leu Asn Glu Ala Ile Ile Pro Lys Thr Glu Met Asn Val
145                 150                 155
```

<210> SEQ ID NO 2
<211> LENGTH: 480
<212> TYPE: DNA
<213> ORGANISM: Human herpesvirus 6

<400> SEQUENCE: 2

```
atgggatatg aagaaaaagt gtcagctact ggaaagactc gtttaaagat actggcatgt      60
ctgatcgttt taatactagc tgcggcaata actatgttaa cgctggaaat tatatcgaac     120
caaaaacgta ccactactga tctcgaagct gtgactgtgg cgctgaagca tgtaagcaca     180
tctcttgcca gctgcactga atccactact tctgtacata ccgattctgt gacgagccaa     240
cccacgaaaa acaaagaatc gaggaaaaaa attgaaggga atctccaag ttgggttcag      300 gctttaacta cagcatctgg aattatccta ctgttttgta atgatgat attcattaca      360 tgttcctgga ccacagaaaa agatacagag aagagtgaag tgcaatctta tgcttcttca     420
```
gtagagactt tagactcttt aaatgaggct attataccga aaactgaaat gaatgtgtaa    480

<210> SEQ ID NO 3
<211> LENGTH: 1795
<212> TYPE: DNA
<213> ORGANISM: Human herpesvirus 6

<400> SEQUENCE: 3
aggctctgct ggaggctctg ctggaggcct tgctgaaggc tctgctggag gccctgctgg    60
aggtcttgct ggaggctctg ctggaggctc tgctggaggc tctgctggag gctctgctgg    120
aggctctgct ggaggctctg ctggaggctc tgtcagagac ctcggtgaaa gttttactca    180
gaggtttatc agagttttcg ccattagttt ggttagaagt ttcagattta ttttcggtgg    240
aactgcagtt aggtttcatg tcagtacatt catcaccgtt agaagtgcta ttcatggtgc    300
tgttgccact gttggatttg ttaaaagcag taaatgagct aggattggaa tgactccgaa    360
tagctaataa atttgagcat tttcttcgaa tggatcataa tcagagggat agccatctaa    420
tttaaagact tccattttat cactgttgca atcacttcta atggagtatc tggatacatt    480
ttttctacat ctttttcatc ccctccaaca tggatctgtg cagcgttaat aagccagcgg    540
agttaattaa atcgtcttcc atgttagaca gttcctgttt catggcagcc ttcactgatg    600
caccaatact ttggatgcaa gtgccaacgg actgagctag gatgtaaaag aagatattct    660
aattttgaat tcttcagatg ctccttcttc cacattactg gaataggaca cattcttgga    720
agcgatgtcg ttggaagact ctgggatgaa aagatcacag gcttccagtt ctggaaaaag    780
caggctttca aaggacacat cacacttgag actctcttcc aatatttctt tgatggattc    840
ttccaccact ggatcgggat ggtagctata tatactatat aaggagatta ccaccaccac    900
ctctttcttt gcagagatta ttctctgctt gaaaatctgt aacactgatc atgatgggat    960
atgaagaaaa agtgtcagct actggaaaga ctcgtttaaa gatactggca tgtctgatcg    1020
ttttaatact agctgcggca ataactatgt taacgctgga aattatatcg aaccaaaaac    1080
gtaccactac tgatctcgaa gctgtgactg tggcgctgaa gcatgtaagc acatctcttg    1140
ccagctgcac tgaatccact acttctgtac ataccgattc tgtgacgagc caacccacga    1200
aaaacaaaga atcgaggaaa aaaattgaag ggaaatctcc aagttgggtt caggctttaa    1260
ctacagcatc tggaattatc ctactgtttt gtataatgat gatattcatt acatgtccct    1320
ggaccacaga aaaagataca gagaagagtg aagtgcaatc ttatgctcct tcagtagaga    1380
ctttagaccc tttaaatgag gctattatac gaaaactga aatgaatgtg taatgtctgt    1440
atttttcttt acagagatgt acggagagtt tatatttggg gaaaatacct gactgttctg    1500
cctatatgcg aatgttaaag tatgtataat ataaattctt acctttaag agtgattcaa    1560
ggtggaggtt tctttggaga ttgattccag gtggtggttt cgggtgcaat caatctttct    1620
tctgggcggg aagaaaatcc agcaatccaa taattgatgg gatgtaatca atgtcacaaa    1680
tctgtaagat taaatgtgaa cagtataaat tctttcgtgc ttatcaaatt acaattatgc    1740
gcatgaaaat atcattaaat tgttttaaac attcttaaaa aaaaaaaaaa aaaaa        1795

<210> SEQ ID NO 4
<211> LENGTH: 25
<212> TYPE: DNA
<213> ORGANISM: Artificial Sequence
<220> FEATURE:
<223> OTHER INFORMATION: Synthetic primer

<400> SEQUENCE: 4

```
gatgctcctt cttccacatt actgg                                          25

<210> SEQ ID NO 5
<211> LENGTH: 26
<212> TYPE: DNA
<213> ORGANISM: Artificial Sequence
<220> FEATURE:
<223> OTHER INFORMATION: Synthetic primer

<400> SEQUENCE: 5
catcccatca attattggat tgctgg                                         26

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6
gaaaccacca cctggaatca atctcc                                         26

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gacacattct tggaagcgat gtcg                                           24

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
gctgggtagt ccccacctttt ctaga                                         25

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9
ctgaagcatg taagcacatc tcttgc                                         26

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
gcttcgagat cagtagtggt acg                                            23
```